(12) United States Patent
Johnson et al.

(10) Patent No.: US 10,994,273 B2
(45) Date of Patent: *May 4, 2021

(54) ACTUATION OF PARALLEL MICROFLUIDIC ARRAYS

(71) Applicant: CYTONOME/ST, LLC, Bedford, MA (US)

(72) Inventors: Andrew Johnson, Randolph, MA (US); John R. Gilbert, Brookline, MA (US); Manish Deshpande, Canton, MA (US); Hugh Lewis, Gravelotte (ZA); Bernard Bunner, Watertown, MA (US)

(73) Assignee: CYTONOME/ST, LLC, Bedford, MA (US)

( * ) Notice: Subject to any disclaimer, the term of this patent is extended or adjusted under 35 U.S.C. 154(b) by 67 days.

This patent is subject to a terminal disclaimer.

(21) Appl. No.: 16/119,404

(22) Filed: Aug. 31, 2018

(65) Prior Publication Data

US 2019/0099755 A1 Apr. 4, 2019

Related U.S. Application Data

(63) Continuation of application No. 15/042,996, filed on Feb. 12, 2016, now Pat. No. 10,065,188, which is a
(Continued)

(51) Int. Cl.
*B01L 3/00* (2006.01)
*C12N 5/00* (2006.01)
*B07C 5/34* (2006.01)

(52) U.S. Cl.
CPC .......... *B01L 3/502761* (2013.01); *B01L 3/52* (2013.01); *B07C 5/34* (2013.01); *C12N 5/0081* (2013.01);
(Continued)

(58) Field of Classification Search
CPC .............. B01L 3/52; B01L 3/502761; B01L 2200/027; B01L 2200/028;
(Continued)

(56) References Cited

U.S. PATENT DOCUMENTS 2,015,522 A 9/1935 Hoffman
2,646,882 A 7/1953 Frost
(Continued)

FOREIGN PATENT DOCUMENTS

DE 102005054923 B3 4/2007
EP 0177718 A2 4/1986
(Continued)

OTHER PUBLICATIONS

Altendorf et al., Differential Blood Cell Counts Obtained Using a Microchannel Based Flow Cytometer. Solid State Sensors & Actuators, vol. 1, 531, 1997.
(Continued)

*Primary Examiner* — Terrell H Matthews
(74) *Attorney, Agent, or Firm* — McCarter & English, LLP; David R. Burns

(57) ABSTRACT

An improved actuator for use in a microfluidic particle sorting system utilizes a staggered packing scheme for a plurality of actuators used to selectively deflect a particle in an associated sorting channel from a stream of channels. An actuator block may be provided for housing a two-dimensional array of actuators, each configured to align with an actuation port in an associated sorting chip containing a plurality of sorting channels. The actuator block may include a built-in stressing means to pre-stress each actuator housed by the block. An actuator comprising a piezo-electric stack may employ contact-based electrical connection rather than soldered wires to improve packing density. The actuator may be an external actuator. That is, the external actuator is
(Continued)

external to the substrate in which the sorting channels are formed.

20 Claims, 13 Drawing Sheets

Related U.S. Application Data continuation of application No. 14/517,396, filed on Oct. 17, 2014, now Pat. No. 9,260,693, which is a continuation-in-part of application No. 14/179,760, filed on Feb. 13, 2014, now Pat. No. 9,823,252, which is a continuation of application No. 13/240,521, filed on Sep. 22, 2011, now Pat. No. 8,679,422, which is a continuation of application No. 11/295,183, filed on Dec. 5, 2005, now Pat. No. 8,277,764, said application No. 14/517,396 is a continuation-in-part of application No. 13/371,277, filed on Feb. 10, 2012, now Pat. No. 8,863,962, which is a continuation of application No. 11/800,469, filed on May 4, 2007, now Pat. No. 8,123,044.

(60) Provisional application No. 60/633,396, filed on Dec. 3, 2004, provisional application No. 60/798,154, filed on May 5, 2006.

(52) U.S. Cl.
CPC ... *B01L 2200/027* (2013.01); *B01L 2200/028* (2013.01); *B01L 2200/0636* (2013.01); *B01L 2200/0652* (2013.01); *B01L 2200/0689* (2013.01); *B01L 2300/021* (2013.01); *B01L 2300/0636* (2013.01); *B01L 2300/0816* (2013.01); *B01L 2300/0864* (2013.01); *B01L 2400/04* (2013.01); *B01L 2400/0439* (2013.01); *B01L 2400/0442* (2013.01); *B01L 2400/0487* (2013.01); *B01L 2400/0622* (2013.01)

(58) Field of Classification Search
CPC ......... B01L 2200/0636; B01L 2400/04; B01L 2400/0439; B07C 5/342
USPC .................................................. 209/552, 559
See application file for complete search history.

(56) References Cited

U.S. PATENT DOCUMENTS

| | | |
|---|---|---|
| 2,787,453 A | 4/1957 | Hibshman et al. |
| 2,850,940 A | 9/1958 | Opperman |
| 2,923,410 A | 2/1960 | Florian |
| 3,289,687 A | 12/1966 | Dunaway |
| 3,362,421 A | 1/1968 | Schaffer |
| 3,370,538 A | 2/1968 | Hines et al. |
| 3,380,584 A | 4/1968 | Fulwyler |
| 3,495,253 A | 2/1970 | Richards |
| 3,506,654 A | 4/1970 | Fried |
| 3,508,654 A | 4/1970 | Glaettli |
| 3,508,655 A | 4/1970 | Kamentsky |
| 3,560,754 A | 2/1971 | Kamentsky |
| 3,785,390 A | 1/1974 | Taylor |
| 3,791,517 A | 2/1974 | Friedman |
| 3,827,555 A | 8/1974 | Kamentsky et al. |
| 3,906,415 A | 9/1975 | Baker |
| 3,984,307 A | 10/1976 | Kamentsky et al. |
| 3,984,621 A | 10/1976 | Propst |
| 4,004,150 A | 1/1977 | Natelson |
| 4,050,851 A | 9/1977 | Haavik |
| 4,147,621 A | 4/1979 | Giddings |
| 4,148,585 A | 4/1979 | Bargeron et al. |
| 4,153,855 A | 5/1979 | Feingold |
| 4,175,662 A | 11/1979 | Zold |
| 4,279,345 A | 7/1981 | Allred |
| 4,284,499 A | 8/1981 | Moudgil et al. |
| 4,318,483 A | 3/1982 | Lombardo et al. |
| 4,344,844 A | 8/1982 | Townley |
| 4,361,400 A | 11/1982 | Gray et al. |
| 4,365,719 A | 12/1982 | Kelly |
| 4,426,451 A | 1/1984 | Columbus |
| 4,445,696 A | 5/1984 | Raj et al. |
| 4,478,076 A | 10/1984 | Bohrer |
| 4,478,077 A | 10/1984 | Bohrer et al. |
| 4,498,353 A | 2/1985 | Kitade |
| 4,498,780 A | 2/1985 | Banno et al. |
| 4,498,782 A | 2/1985 | Proctor et al. |
| 4,501,144 A | 2/1985 | Higashi et al. |
| 4,526,276 A | 7/1985 | Shoor et al. |
| 4,554,427 A | 11/1985 | Flick et al. |
| 4,560,865 A | 12/1985 | Bergstrom |
| 4,572,664 A | 2/1986 | Hanson |
| 4,579,173 A | 4/1986 | Rosensweig et al. |
| 4,581,624 A | 4/1986 | O'Connor |
| 4,636,149 A | 1/1987 | Brown |
| 4,651,564 A | 3/1987 | Johnson et al. |
| 4,676,274 A | 6/1987 | Brown |
| 4,723,129 A | 2/1988 | Endo et al. |
| 4,756,427 A | 7/1988 | Gohde et al. |
| 4,797,696 A | 1/1989 | Allen et al. |
| 4,808,079 A | 2/1989 | Crowley et al. |
| 4,863,588 A | 9/1989 | Herron |
| 4,908,112 A | 3/1990 | Pace |
| 4,936,465 A | 6/1990 | Zold |
| 4,939,081 A | 7/1990 | Figdor et al. |
| 4,954,715 A | 9/1990 | Zold |
| 4,963,498 A | 10/1990 | Hillman et al. |
| 4,983,038 A | 1/1991 | Ohki et al. |
| 4,987,432 A | 1/1991 | Landwehr |
| 5,005,639 A | 4/1991 | Leland |
| 5,030,002 A | 7/1991 | North, Jr. |
| 5,040,890 A | 8/1991 | North, Jr. |
| 5,050,429 A | 9/1991 | Nishimoto et al. |
| 5,053,344 A | 10/1991 | Zborowski et al. |
| 5,065,978 A | 11/1991 | Albarda et al. |
| 5,082,242 A | 1/1992 | Bonne et al. |
| 5,092,972 A | 3/1992 | Ghowsi |
| 5,101,978 A | 4/1992 | Marcus |
| 5,108,623 A | 4/1992 | Cangelosi et al. |
| 5,171,132 A | 12/1992 | Miyazaki et al. |
| 5,176,358 A | 1/1993 | Bonne et al. |
| 5,193,688 A | 3/1993 | Giddings |
| 5,213,479 A | 5/1993 | Dardis et al. |
| 5,216,488 A | 6/1993 | Tguunanen et al. |
| 5,238,223 A | 8/1993 | Mettner et al. |
| 5,244,537 A | 9/1993 | Ohnstein |
| 5,265,327 A | 11/1993 | Faris et al. |
| 5,271,724 A | 12/1993 | van Lintel |
| 5,275,787 A | 1/1994 | Yuguchi et al. |
| 5,277,556 A | 1/1994 | van Lintel |
| 5,307,144 A | 4/1994 | Hiroshi et al. |
| 5,323,999 A | 6/1994 | Bonne et al. |
| 5,395,588 A | 3/1995 | North, Jr. et al. |
| 5,441,597 A | 8/1995 | Bonne et al. |
| 5,483,469 A | 1/1996 | Van den Engh et al. |
| 5,486,335 A | 1/1996 | Wilding et al. |
| 5,489,506 A | 2/1996 | Crane |
| 5,498,392 A | 3/1996 | Wilding et al. |
| 5,519,635 A | 5/1996 | Miyake et al. |
| 5,541,072 A | 7/1996 | Wang et al. |
| 5,608,519 A | 3/1997 | Gourley et al. |
| 5,617,955 A | 4/1997 | Tanner |
| 5,622,831 A | 4/1997 | Liberti et al. |
| 5,632,935 A | 5/1997 | Yeoman et al. |
| 5,637,496 A | 6/1997 | Thaler et al. |
| 5,644,388 A | 7/1997 | Maekawa et al. |
| 5,683,159 A | 11/1997 | Johnson |
| 5,699,157 A | 12/1997 | Parce |
| 5,699,462 A | 12/1997 | Fouquet et al. |
| 5,716,852 A | 2/1998 | Yager et al. |
| 5,726,026 A | 3/1998 | Wilding et al. |
| 5,726,404 A | 3/1998 | Brody |

(56) References Cited

U.S. PATENT DOCUMENTS

| | | |
|---|---|---|
| 5,726,751 A | 3/1998 | Altendorf et al. |
| 5,757,476 A | 5/1998 | Nakamoto et al. |
| 5,777,649 A | 7/1998 | Otsuka et al. |
| 5,783,446 A | 7/1998 | Saul et al. |
| 5,789,045 A | 8/1998 | Wapner et al. |
| 5,795,727 A | 8/1998 | Bierre et al. |
| 5,799,030 A | 8/1998 | Brenner |
| 5,822,170 A | 10/1998 | Cabuz et al. |
| 5,836,750 A | 11/1998 | Cabuz |
| 5,837,200 A | 11/1998 | Diessel et al. |
| 5,851,488 A | 12/1998 | Saul et al. |
| 5,858,195 A | 1/1999 | Ramsey |
| 5,863,502 A | 1/1999 | Southgate et al. |
| 5,876,187 A | 3/1999 | Forster et al. |
| 5,876,266 A | 3/1999 | Miller et al. |
| 5,885,470 A | 3/1999 | Parce et al. |
| 5,893,722 A | 4/1999 | Hibbs-Brenner et al. |
| 5,922,210 A | 7/1999 | Brody et al. |
| 5,922,591 A | 7/1999 | Anderson et al. |
| 5,932,100 A | 8/1999 | Yager et al. |
| 5,948,684 A | 9/1999 | Weigl et al. |
| 5,971,158 A | 10/1999 | Yager et al. |
| 5,972,710 A | 10/1999 | Weigl et al. |
| 5,974,867 A | 11/1999 | Forster et al. |
| 5,976,336 A | 11/1999 | Dubrow et al. |
| 5,979,664 A | 11/1999 | Brodeur |
| 5,988,522 A | 11/1999 | Glezer et al. |
| 5,992,820 A | 11/1999 | Fare et al. |
| 5,998,212 A | 12/1999 | Corio et al. |
| 6,007,775 A | 12/1999 | Yager |
| 6,033,191 A | 3/2000 | Kamper et al. |
| 6,042,709 A | 3/2000 | Parce et al. |
| 6,046,056 A | 4/2000 | Parce et al. |
| 6,048,328 A | 4/2000 | Haller et al. |
| 6,048,734 A | 4/2000 | Burns et al. |
| 6,057,111 A | 5/2000 | Deiss et al. |
| 6,062,681 A | 5/2000 | Field et al. |
| 6,068,751 A | 5/2000 | Neukermans |
| 6,068,752 A | 5/2000 | Dubrow et al. |
| 6,082,185 A | 7/2000 | Saaski |
| 6,086,740 A | 7/2000 | Kennedy |
| 6,097,485 A | 8/2000 | Lievan |
| 6,102,530 A | 8/2000 | Kim et al. |
| 6,103,199 A | 8/2000 | Bjornson et al. |
| 6,120,666 A | 9/2000 | Jacobson et al. |
| 6,145,247 A | 11/2000 | McKinnis |
| 6,152,181 A | 11/2000 | Wapner et al. |
| 6,184,029 B1 | 2/2001 | Wilding et al. |
| 6,193,471 B1 | 2/2001 | Paul |
| 6,196,525 B1 | 3/2001 | Ganan-Calvo |
| 6,197,575 B1 | 3/2001 | Griffith et al. |
| 6,203,291 B1 | 3/2001 | Stemme et al. |
| 6,214,556 B1 | 4/2001 | Olek et al. |
| 6,221,226 B1 | 4/2001 | Kopf-Sill |
| 6,221,654 B1 | 4/2001 | Quake et al. |
| 6,273,553 B1 | 8/2001 | Kim et al. |
| 6,280,967 B1 | 8/2001 | Ransom et al. |
| 6,316,781 B1 | 11/2001 | Nagle et al. |
| 6,318,970 B1 | 11/2001 | Backhouse |
| 6,325,114 B1 | 12/2001 | Bevirt et al. |
| 6,337,740 B1 | 1/2002 | Parce |
| 6,353,475 B1 | 3/2002 | Jensen et al. |
| 6,360,775 B1 | 3/2002 | Barth et al. |
| 6,361,672 B1 | 3/2002 | Zhu et al. |
| 6,431,212 B1 | 8/2002 | Hayenga et al. |
| 6,432,630 B1 | 8/2002 | Blankenstein |
| 6,440,725 B1 | 8/2002 | Pourahmadi et al. |
| 6,454,862 B1 | 9/2002 | Yoshida et al. |
| 6,455,280 B1 | 9/2002 | Edwards et al. |
| 6,481,453 B1 | 11/2002 | O'Connor et al. |
| 6,482,652 B2 | 11/2002 | Furlong et al. |
| 6,488,897 B2 | 12/2002 | Dubrow et al. |
| 6,496,260 B1 | 12/2002 | Hafeman et al. |
| 6,504,607 B2 | 1/2003 | Jensen et al. |
| 6,506,609 B1 | 1/2003 | Wada et al. |
| 6,507,391 B2 | 1/2003 | Riley et al. |
| 6,524,790 B1 | 2/2003 | Kopf-Sill et al. |
| 6,532,061 B2 | 3/2003 | Ortyn et al. |
| 6,534,011 B1 | 3/2003 | Karthe et al. |
| 6,540,895 B1 | 4/2003 | Spence et al. |
| 6,561,224 B1 | 5/2003 | Cho |
| 6,567,163 B1 | 5/2003 | Sandstrom |
| 6,592,821 B1 | 7/2003 | Wada et al. |
| 6,597,438 B1 | 7/2003 | Cabuz et al. |
| 6,602,702 B1 | 8/2003 | McDevitt et al. |
| 6,616,823 B2 | 9/2003 | Kopf-Sill |
| 6,629,820 B2 | 10/2003 | Kornelsen |
| 6,632,400 B1 | 10/2003 | Brennen et al. |
| 6,649,403 B1 | 11/2003 | McDevitt et al. |
| 6,657,730 B2 | 12/2003 | Pfau et al. |
| 6,674,525 B2 | 1/2004 | Bardell et al. |
| 6,703,205 B2 | 3/2004 | Kopf-Sill et al. |
| 6,739,576 B2 | 5/2004 | O'Connor et al. |
| 6,744,038 B2 | 6/2004 | Wang et al. |
| 6,747,285 B2 | 6/2004 | Schueller et al. |
| 6,756,019 B1 | 6/2004 | Dubrow et al. |
| 6,759,662 B1 | 7/2004 | Li |
| 6,767,706 B2 | 7/2004 | Quake et al. |
| 6,771,421 B2 | 8/2004 | Rope et al. |
| 6,799,681 B1 | 10/2004 | Warren |
| 6,802,342 B2 | 10/2004 | Fernandes et al. |
| 6,803,194 B1 | 10/2004 | Keck et al. |
| 6,808,075 B2 | 10/2004 | Bohm et al. |
| 6,821,484 B1 | 11/2004 | Gregersen |
| 6,830,936 B2 | 12/2004 | Anderson et al. |
| 6,838,056 B2 | 1/2005 | Foster |
| 6,877,528 B2 | 4/2005 | Gilbert et al. |
| 6,883,957 B2 | 4/2005 | Gilbert et al. |
| 6,930,314 B2 | 8/2005 | Jackson, III et al. |
| 6,976,590 B2 | 12/2005 | Deshpande et al. |
| 6,980,303 B2 | 12/2005 | Kume et al. |
| 7,024,281 B1 | 4/2006 | Unno |
| 7,069,943 B2 | 7/2006 | Gilbert et al. |
| 7,075,652 B1 | 7/2006 | Sarvazyan et al. |
| 7,080,664 B1 | 7/2006 | Ayer |
| 7,104,405 B2 | 9/2006 | Bohm et al. |
| 7,118,910 B2 | 10/2006 | Unger et al. |
| 7,157,274 B2 * | 1/2007 | Bohm .................. B07C 5/34 209/172.5 |
| 7,157,275 B2 | 1/2007 | Guarino et al. |
| 7,220,594 B2 | 5/2007 | Foster et al. |
| 7,242,474 B2 | 7/2007 | Cox et al. |
| 7,258,774 B2 | 8/2007 | Chou et al. |
| 7,298,478 B2 * | 11/2007 | Gilbert ............... G01N 15/1484 356/338 |
| 7,303,727 B1 | 12/2007 | Dubrow et al. |
| 7,312,085 B2 | 12/2007 | Chou et al. |
| 7,355,699 B2 | 4/2008 | Gilbert et al. |
| 7,389,879 B2 | 6/2008 | Tyvoll et al. |
| 7,419,784 B2 | 9/2008 | Dubrow et al. |
| 7,452,725 B2 | 11/2008 | Leary et al. |
| 7,476,363 B2 | 1/2009 | Unger et al. |
| 7,497,334 B2 | 3/2009 | Tyvoll et al. |
| 7,569,788 B2 | 8/2009 | Deshpande et al. |
| 7,584,857 B2 | 9/2009 | Bohm et al. |
| 7,612,355 B2 | 11/2009 | Wu et al. |
| 7,612,871 B2 | 11/2009 | Cox et al. |
| 7,641,856 B2 | 1/2010 | Padmanabhan et al. |
| 7,802,686 B2 | 9/2010 | Takagi et al. |
| 7,820,427 B2 | 10/2010 | Unger et al. |
| 7,863,035 B2 | 1/2011 | Clemens et al. |
| 7,963,399 B2 | 6/2011 | Bohm et al. |
| 7,964,078 B2 | 6/2011 | Lee et al. |
| 8,123,044 B2 | 2/2012 | Johnson et al. |
| 8,210,209 B2 | 7/2012 | Gilbert et al. |
| 8,252,604 B2 | 8/2012 | Rigler |
| 8,268,245 B2 | 9/2012 | Wahl |
| 8,277,764 B2 | 10/2012 | Gilbert et al. |
| 8,408,399 B2 | 4/2013 | Bohm et al. |
| 8,567,608 B2 | 10/2013 | Deshpande et al. |
| 8,609,039 B2 | 12/2013 | Zhou et al. |
| 8,623,294 B2 | 1/2014 | Asogawa et al. |
| 8,623,295 B2 | 1/2014 | Gilbert et al. |
| 8,678,192 B1 | 3/2014 | Pung et al. |

(56) References Cited

U.S. PATENT DOCUMENTS

| | | |
|---|---|---|
| 8,679,422 B2 | 3/2014 | Gilbert et al. |
| 8,691,164 B2* | 4/2014 | Butler .................... C12M 47/04 |
| | | 422/505 |
| 8,723,140 B2 | 5/2014 | Kiesel et al. |
| 8,727,131 B2 | 5/2014 | Desphande et al. |
| 8,844,571 B2 | 9/2014 | Golling et al. |
| 8,863,962 B2 | 10/2014 | Johnson et al. |
| 8,895,311 B1 | 11/2014 | Handique et al. |
| 9,011,797 B2 | 4/2015 | Gilbert et al. |
| 9,074,978 B2 | 7/2015 | Lo et al. |
| 9,149,806 B2 | 10/2015 | Collins |
| 9,194,786 B2 | 11/2015 | Foster et al. |
| 9,260,693 B2* | 2/2016 | Johnson .................... B01L 3/52 |
| 9,339,850 B2 | 5/2016 | Deshpande et al. |
| 9,448,157 B2 | 9/2016 | Ito |
| 9,550,215 B2 | 1/2017 | Deshpande et al. |
| 9,757,726 B2* | 9/2017 | Sharpe ............... G01N 15/1459 |
| 9,823,252 B2 | 11/2017 | Gilbert et al. |
| 10,029,263 B2 | 7/2018 | Bohm et al. |
| 10,029,283 B2 | 7/2018 | Deshpande et al. |
| 10,065,188 B2 | 9/2018 | Johnson et al. |
| 10,222,378 B2 | 3/2019 | Gilbert et al. |
| 10,794,913 B2 | 10/2020 | Gilbert et al. |
| 2001/0054702 A1 | 12/2001 | Williams |
| 2002/0005354 A1 | 1/2002 | Spence et al. |
| 2002/0055167 A1 | 5/2002 | Pourahmadi et al. |
| 2002/0058332 A1 | 5/2002 | Quake et al. |
| 2002/0071121 A1 | 6/2002 | Ortyn et al. |
| 2002/0093641 A1 | 7/2002 | Ortyn et al. |
| 2002/0122167 A1 | 9/2002 | Riley et al. |
| 2002/0124896 A1 | 9/2002 | O'Connor et al. |
| 2002/0132315 A1 | 9/2002 | Wang et al. |
| 2002/0166585 A1 | 11/2002 | O'Connor et al. |
| 2002/0177135 A1 | 11/2002 | Doung et al. |
| 2003/0027225 A1 | 2/2003 | Wada et al. |
| 2003/0096430 A1 | 5/2003 | Holl et al. |
| 2003/0138941 A1 | 7/2003 | Gong et al. |
| 2003/0196714 A1 | 10/2003 | Gilbert et al. |
| 2003/0198523 A1 | 10/2003 | Bohm et al. |
| 2004/0011650 A1 | 1/2004 | Zenhausern et al. |
| 2004/0017570 A1 | 1/2004 | Parikh et al. |
| 2004/0037739 A1 | 2/2004 | McNeely et al. |
| 2004/0050866 A1 | 3/2004 | Ingenhoven et al. |
| 2004/0086872 A1 | 5/2004 | Childers et al. |
| 2004/0115094 A1 | 6/2004 | Gumbrecht et al. |
| 2004/0161772 A1 | 8/2004 | Bohm et al. |
| 2004/0180426 A1 | 9/2004 | Maher et al. |
| 2004/0233424 A1 | 11/2004 | Lee et al. |
| 2005/0183995 A1 | 8/2005 | Deshpande et al. |
| 2006/0170912 A1 | 8/2006 | Mueth et al. |
| 2006/0177348 A1 | 8/2006 | Yasuda et al. |
| 2006/0278288 A1 | 12/2006 | Gilbert et al. |
| 2007/0065808 A1 | 3/2007 | Bohm et al. |
| 2007/0076199 A1 | 4/2007 | Ode |
| 2008/0030865 A1 | 2/2008 | Gilbert et al. |
| 2008/0070311 A1 | 3/2008 | Li |
| 2008/0124779 A1* | 5/2008 | Oh ......................... B03C 1/32 |
| | | 435/173.9 |
| 2008/0180666 A1 | 7/2008 | Gilbert et al. |
| 2008/0182338 A1 | 7/2008 | Abraham-Fuchs et al. |
| 2008/0213821 A1 | 9/2008 | Liu et al. |
| 2009/0283452 A1 | 11/2009 | Lean et al. |
| 2010/0032350 A1 | 2/2010 | Deshpande et al. |
| 2010/0133151 A1 | 6/2010 | Bohm et al. |
| 2011/0005978 A1 | 1/2011 | Bohm et al. |
| 2011/0030808 A1 | 2/2011 | Chiou et al. |
| 2012/0006727 A1 | 1/2012 | Bohm et al. |
| 2012/0012508 A1 | 1/2012 | Deshpande et al. |
| 2012/0015442 A1 | 1/2012 | Gilbert et al. |
| 2012/0153185 A1 | 6/2012 | Ito et al. |
| 2012/0258488 A1 | 10/2012 | Abilez et al. |
| 2013/0083315 A1 | 4/2013 | Lo et al. |
| 2014/0251879 A1 | 9/2014 | Deshpande et al. |
| 2014/0273192 A1* | 9/2014 | Sharpe ............... G01N 15/1459 |
| | | 435/288.7 |
| 2014/0318645 A1* | 10/2014 | Koksal ............. B01L 3/502776 |
| | | 137/559 |
| 2014/0339445 A1 | 11/2014 | Sharpe et al. |
| 2015/0268244 A1* | 9/2015 | Cho ................... G01N 15/1463 |
| | | 435/7.23 |
| 2015/0298122 A1 | 10/2015 | Zeng et al. |
| 2015/0328637 A1* | 11/2015 | Perrault, Jr. ...... B01L 3/502738 |
| | | 435/287.1 |
| 2015/0352597 A1 | 12/2015 | Deshpande et al. |
| 2015/0375227 A1 | 12/2015 | Quake et al. |
| 2016/0040226 A1 | 2/2016 | Mehta et al. |
| 2016/0158758 A1 | 6/2016 | Johnson et al. |
| 2019/0195876 A1 | 6/2019 | Gilbert et al. |

FOREIGN PATENT DOCUMENTS

| | | |
|---|---|---|
| EP | 0644417 A1 | 3/1995 |
| EP | 0745682 A1 | 12/1996 |
| EP | 0793098 A1 | 9/1997 |
| EP | 1001326 A1 | 5/2000 |
| EP | 1065378 A2 | 1/2001 |
| FR | 2865145 A1 | 7/2005 |
| GB | 2140128 A | 11/1984 |
| GB | 2229649 A | 10/1990 |
| JP | S49-046274 A | 5/1974 |
| JP | 60-153023 | 8/1985 |
| JP | S61-137062 A | 6/1986 |
| JP | S63-259466 A | 10/1988 |
| JP | H01-170853 A | 7/1989 |
| JP | H03-043070 A | 2/1991 |
| JP | H05-506180 A | 9/1993 |
| JP | H06-507241 A | 8/1994 |
| JP | 07-167798 | 7/1995 |
| JP | H08-332074 A | 12/1996 |
| JP | H09-141124 A | 6/1997 |
| JP | H09-509498 A | 9/1997 |
| JP | 11-108838 | 4/1999 |
| JP | H11-508182 A | 7/1999 |
| JP | 2001-515216 A | 9/2001 |
| JP | 2001-520377 A | 10/2001 |
| JP | 2001-521755 A | 11/2001 |
| JP | 2001-527220 A | 12/2001 |
| JP | 2002-503334 A | 1/2002 |
| JP | 2004-505272 A | 2/2004 |
| JP | 2005-521786 A | 7/2005 |
| JP | 2005-524831 A | 8/2005 |
| JP | 2005-534896 A | 11/2005 |
| JP | 2006-521786 A | 9/2006 |
| WO | 1991/014505 A1 | 10/1991 |
| WO | 1991/015750 A1 | 10/1991 |
| WO | 1995/27199 A1 | 10/1995 |
| WO | 1997/002357 A1 | 1/1997 |
| WO | 1998/000231 A1 | 1/1998 |
| WO | 1998/007069 A1 | 2/1998 |
| WO | 1998/010267 A1 | 3/1998 |
| WO | 1998/052691 A1 | 11/1998 |
| WO | 1999/19717 A1 | 4/1999 |
| WO | 1999/023471 A1 | 5/1999 |
| WO | 1999/043432 A1 | 9/1999 |
| WO | 1999/60397 A1 | 11/1999 |
| WO | 2000/06996 A1 | 2/2000 |
| WO | 2000/070080 A1 | 11/2000 |
| WO | 2001/02846 A1 | 1/2001 |
| WO | 2001/09598 A1 | 2/2001 |
| WO | 2001/026813 A2 | 4/2001 |
| WO | 2002/004689 A1 | 1/2002 |
| WO | 2002/010713 A2 | 2/2002 |
| WO | 2002/029106 A2 | 4/2002 |
| WO | 2001/45843 A9 | 5/2002 |
| WO | 2003/089158 A1 | 10/2003 |
| WO | 2003/104772 A1 | 12/2003 |
| WO | 2003/035229 A3 | 1/2004 |

(56) References Cited

FOREIGN PATENT DOCUMENTS

WO     2004/039500 A1     5/2004
WO     2004/069983 A3     7/2005

OTHER PUBLICATIONS

Altendorf et al., Results Obtained Using a Prototype Microfluidics-Based Hematology Analyzer. Micro Total Analysis Systems '98. Proceedings of the uTAS '98 Workshop, held in Banff, Canada, Oct. 13-16, 1998, pp. 73-76.
Darling et al., Integration of Microelectrodes With Etched Microchannels for In-Stream Electrochemical Analysis. Micro Total Analysis Systems '98, D.J. Harrison (Ed.), Kluwer Academic Publishers. Apr. 1998, pp. 105-108.
Shapiro, Practical Flow Cytometry, Third Edition. Wiley-Liss, Inc., New York. 276 pages. (1995).
Weigl et al., Diffusion-Based Optical Chemical Detection in Silicon Flow Structures. Analytical Methods & Instrumentation. .mu.TTAS 96 special edition, 22 pages, (1996).
Weigl et al., Fluorescence and Absorbance Analyte Sensing in Whole Blood and Plasma Based on Diffusion Separation in Silicon-Microfabricated Flow Structures. In Advances in Fluorescence Sensing Technology III. SPIE Proceedings. 2980. May 7, 1997; pp. 171-181.
Weigl et al., Microfluidic Diffusion Based Separation and Detection. Science. Jan. 15, 1999;283(5400):346-347.
Weigl et al., Silicon-Microfabricated Diffusion-Based Optical Chemical Sensor. Sensors and Actuators B: Chemical. Mar.-Apr. 1997;39(1-3):452-457.
Weigl et al., Simultaneous Self-Referencing Analyte Determination in Complex Sample Solutions Using Microfabricated Flow Structures (T-Sensors.TM.). Proceedings of MicroTAS, Banff, Canada, Oct. 1998, pp. 81-84.
Yager et al., Design of Microfluidic Sample Preconditioning Systems for Detection of Biological Agents in Environmental Samples. SPIE Proceedings Microfluidic Devices and Systems, Abstract 3515, pp. 252-259, Sep. 10, 1998.
Australian Office Action for Application No. 2005311631, dated Aug. 27, 2010, 2 pages.
Brazilian Examination Report for Application No. PI 0518824-5, dated Apr. 11, 2017.
Canadian Office Action for Application No. 2,588,753, dated Oct. 30, 2012.
Canadian Office Action for Application No. 2,651,250, dated Mar. 5, 2015.
Canadian Office Action for Application No. 2,651,250, dated May 16, 2014.
Chinese Office Action for Application No. 200580046282.8, dated Dec. 21, 2011.
Chinese Office Action for Application No. 200780019958.3, dated Feb. 2, 2012.
European Office Action for Application No. 05853002.3, dated Jan. 19, 2009.
European Search Report for Application No. 11151431.1, dated May 2, 2012.
Indian Office Action for Application No. 2093/KOLNP/2007, dated Dec. 8, 2014.
International Search Report for Application No. PCT/US2005/043965, dated Jul. 12, 2006.
International Search Report for Application No. PCT/US2007/010959, dated Aug. 8, 2008.
Invitation to Pay Additional Fees for Application No. PCT/US2005/043965, dated Mar. 20, 2006.
Invitation to Pay Additional Fees for Application No. PCT/US2007/010959, dated Feb. 1, 2008.
Japanese Office Action for Application No. 2007-544599, dated Jan. 28, 2013.
Japanese Office Action for Application No. 2007-544599, dated Oct. 19, 2011.
United States Office Action for U.S. Appl. No. 11/285,183, dated Sep. 27, 2011.
United States Office Action for U.S. Appl. No. 13/240,521, dated Jun. 7, 2012.
Adkins et al., Development of an electromagnetically actuated mercury microvalve. MEMS. Aug. 1998;66:133-7.
Bottausci et al., Mixing in the shear superposition micromixer: three-dimensional analysis. Philos Trans a Math Phys Eng Sci. May 15, 2004;362(1818):1001-18.
Carter et al., Introduction to the principles of flow cytometry. Chapter 1, Flow Cytometry, 3rd Edition. Oxford University Press, 2002.
Chapman. Instrumentation for flow cytometry. J Immunol Methods. Sep. 21, 2000;243(1-2):3-12.
Claim Construction Order Regarding U.S. Pat. Nos. 6,877,528, No. 8,623,295, 9,011,797, 9,339,850, 10,029,263, 10,029,283, and U.S. Pat. No. 10,065,188. *Cytonome/St, LLC* v *Nanocellect Biomedical, Inc.* Case No. 19-cv-301. 4 pages, dated Jun. 2, 2020.
Cytonome/St, LLC's Preliminary Response, *Nanocellect Biomedical, Inc.*, v. *Cytonome/St, LLC*. Case IPR2020-00551, U.S. Pat. No. 10,065,188. 25 pages, Jun. 1, 2020.
Davey et al., Flow cytometry and cell sorting of heterogeneous microbial populations: the importance of single-cell analyses. Microbiol Rev. Dec. 1996;60(4):641-96.
Decision Denying Institution of Inter Partes Review, 35 U.S.C. § 314, 37 C.F.R. § 42.4. *Nanocellect Biomedical, Inc.* v. *Cytonome/St, LLC*. Case IPR2020-00547, U.S. Pat. No. 10,029,283 B2. Entered Aug. 24, 2020. 19 pages.
Decision Denying Institution of Inter Partes Review, 35 U.S.C. § 314, 37 C.F.R. § 42.4. *Nanocellect Biomedical, Inc.* v. *Cytonome/St, LLC*. Case IPR2020-00549, U.S. Pat. No. 10,029,263 B2. Entered Aug. 24, 2020. 19 pages.
Decision Denying Institution of Inter Partes Review, 35 U.S.C. § 314, 37 C.F.R. § 42.4. *Nanocellect Biomedical, Inc.* vs. *Cytonome/St, LLC*. Case IPR2020-00545, U.S. Pat. No. 6,877,528 B2. Entered Aug. 24, 2020. 21 pages.
Decision Denying Institution of Inter Partes Review, 35 U.S.C. § 314, 37 C.F.R. § 42.4. *Nanocellect Biomedical, Inc.* vs. *Cytonome/St, LLC*. Case IPR2020-00546, U.S. Pat. No. 9,339,850 B2. Entered Aug. 31, 2020. 33 pages.
Decision Denying Institution of Inter Partes Review, 35 U.S.C. § 314, 37 C.F.R. § 42.4. *Nanocellect Biomedical, Inc.* vs. *Cytonome/St, LLC*. Case IPR2020-00548, U.S. Pat. No. 8,623,295. Entered Sep. 1, 2020. 32 pages.
Decision Denying Institution of Inter Partes Review, 35 U.S.C. § 314, 37 C.F.R. § 42.4. *Nanocellect Biomedical, Inc.* vs. *Cytonome/St, LLC*. Case IPR2020-00550, U.S. Pat. No. 9,011,797. Entered Sep. 1, 2020. 35 pages.
Decision, *Nanocellect Biomedical, Inc.*, v. *Cytonome/St, LLC*. IPR2020-00551, U.S. Pat. No. 10,065,188. 46 pages, Aug. 27, 2020.
Declaration of Bernhard H. Weigl. *Nanocellect Biomedical, Inc.* v. *Cytonome/St, LLC*. Case IPR2020-00551, U.S. Pat. No. 10,065,188. Feb. 12, 2020. 147 pages.
Declaration of Dr. Giacomo Vacca, *Cytonome/St, LLC*, v. *Nanocellect Biomedical, Inc.* C.A. No. 19-301 (RGA). 21 pages, Jan. 31, 2020.
Defendant/Counterclaim-Plaintiff Nanocellect Biomedical, Inc.'s Initial Invalidity Contentions Regarding U.S. Pat. Nos. 6,877,528, 8,623,295, 9,011,797, 9,339,850, 10,029,263, 10,029,283, and U.S. Pat. No. 10,065,188. *Cytonome/St, LLC* v *Nanocellect Biomedical, Inc.* Case No. 19-cv-301. 46 pp., dated Sep. 20, 2019.
Defendant/Counterclaim-Plaintiff Nanocellect Biomedical, Inc.'s Second Supplemental Invalidity Contentions Regarding U.S. Pat. Nos. 6,877,528, 8,623,295, 9,011,797, 9,339,850, 10,029,263, 10,029,283, and U.S. Pat. No. 10,065,188. *Cytonome/St, LLC* v *Nanocellect Biomedical, Inc.* Case No. 19-cv-301. 32 pp., dated Aug. 10, 2020.
Defendant/Counterclaim-Plaintiff Nanocellect Biomedical, Inc.'s Supplemental Invalidity Contentions Regarding U.S. Pat. Nos. 6,877,528, 8,623,295, 9,011,797, 9,339,850, 10,029,263, 10,029,283, and U.S. Pat. No. 10,065,188. *Cytonome/St, LLC* v *Nanocellect Biomedical, Inc.* Case No. 19-cv-301. 49 pp., dated Aug. 3, 2020.

(56) References Cited

OTHER PUBLICATIONS

Deshpande et al., Novel designs for electrokinetic injection in Mu-TAS. Micro Total Analysis Systems. 2000;339-42.

Figeys et al., Lab-on-a-chip: a revolution in biological and medical sciences. Anal Chem. May 1, 2000;72(9):330A-5A.

Fu et al., A microfabricated fluorescence-activated cell sorter. Nat Biotechnol. Nov. 1999;17(11):1109-11.

Fu et al., An integrated microfabricated cell sorter. Anal Chem. Jun. 1, 2002;74(11):2451-7.

Furlan et al., Behavior of micro fluidic amplifiers. Sens Actuat A. 1996;51:239-46.

Hosokawa et al., Study of MHD (Magnetohydrodynamic) micropump. Paper No. 92-0446. 1993;205-10. 6 pages with English abstract.

Joint Claim Construction Brief. *Cytonome/St, LLC v Nanocellect Biomedical, Inc.* Case No. 19-cv-301. 93 pages, dated Feb. 21, 2020.

Madou. Fundamentals of Microfabrication: The Science of Miniaturization. CRC Press, 2nd Edition. 2001;1-13,470-75,551-6.

Memorandum Opinion Regarding U.S. Pat. Nos. 6,877,528, 8,623,295, 9,011,797, 9,339,850, 10,029,263, 10,029,283, and U.S. Pat. No. 10,065,188. *Cytonome/St, LLC v Nanocellect Biomedical, Inc.* Case No. 19-cv-301. 9 pp., dated May 26, 2020.

Opening Expert Report of Dr. Carl Meinhart (Redacted). *Cytonome/St, LLC v Nanocellect Biomedical, Inc.* Case No. 19-cv-301. 263 Pages.

Petition for Inter Partes Review of U.S. Pat. No. 10,029,263, *Nanocellect Biomedical, Inc. v. Cytonome/St, LLC*, Case No. IPR2020-00549, 95 pages, Feb. 11, 2020.

Petition for Inter Partes Review of U.S. Pat. No. 10,029,283, *Nanocellect Biomedical, Inc. v. Cytonome/St, LLC*, Case No. IPR2020-00547, 73 pages, Feb. 12, 2020.

Petition for Inter Partes Review of U.S. Pat. No. 10,065,188, *Nanocellect Biomedical, Inc.,* v. *Cytonome/St, LLC*. Case No. IPR2020-00551, U.S. Pat. No. 10,065,188. 89 pages. Feb. 12, 2020.

Petition for Inter Partes Review of U.S. Pat. No. 6,877,528, *Nanocellect Biomedical, Inc.* v. *Cytonome/St, LLC*, Case No. IPR2020-00545, 85 pages, Feb. 10, 2020.

Petition for Inter Partes Review. Case IPR2019-00550, U.S. Pat. No. 9,011,797. *Nanocellect Biomedical, Inc.* vs. *Cytonome/St, LLC*. Feb. 12, 2020. 86 pages.

Petition for Inter Partes Review. Case IPR2020-00546, U.S. Pat. No. 9,339,850. *Nanocellect Biomedical, Inc.* vs. *Cytonome/St, LLC*. Feb. 11, 2020. 83 pages Petition for Inter Partes Review. Case IPR2020-00548, U.S. Pat. No. 8,623,295. *Nanocellect Biomedical, Inc.* vs. *Cytonome/St, LLC*. Feb. 12, 2020. 78 pages.

Tas et al., Bubble pump for integrated nanofluidics. IEEE-NANO. T2.2. Oct. 30, 2001;454-8.

Veenstra et al., The design of an in-plane compliance structure for microfluidical systems. Sens Actuat B. 2002;81:377-83.

Volpert et al., Modeling and numerical analysis of mixing in an actively controlled micromixer. HEFAT 2002, Proceedings of the First International Conference on Heat Transfer, Fluid Mechanics and Thermodynamics. vol. 1, Part 1, pp. 380-385, Apr. 8-10, 2002.

Zeng et al., Fabrication and characterization of electroosmotic micropumps. Sens Actuat B. 2001;79:107-14.

Zengerle et al., Simulation of microfluid systems. J Micromech Microeng. 1994;4:192-204.

\* cited by examiner

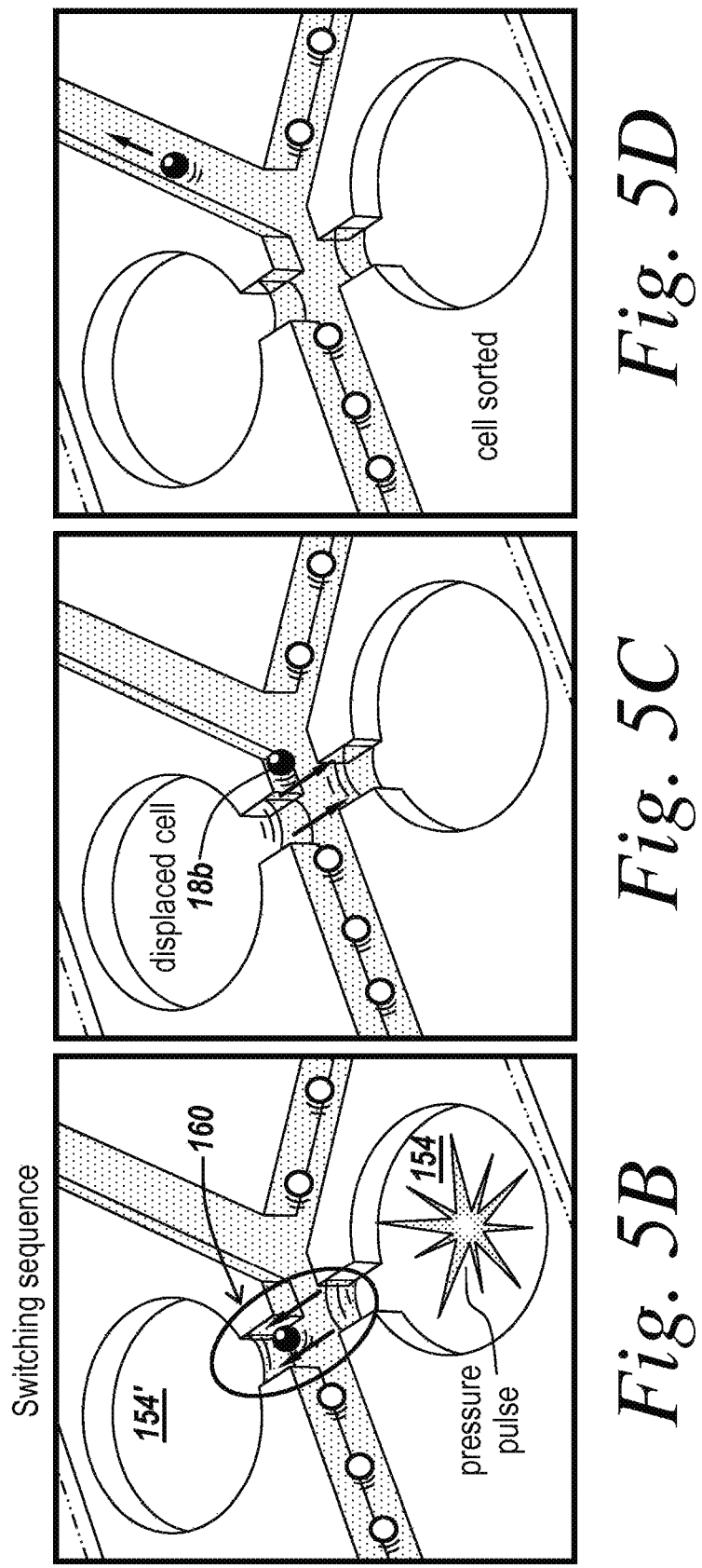

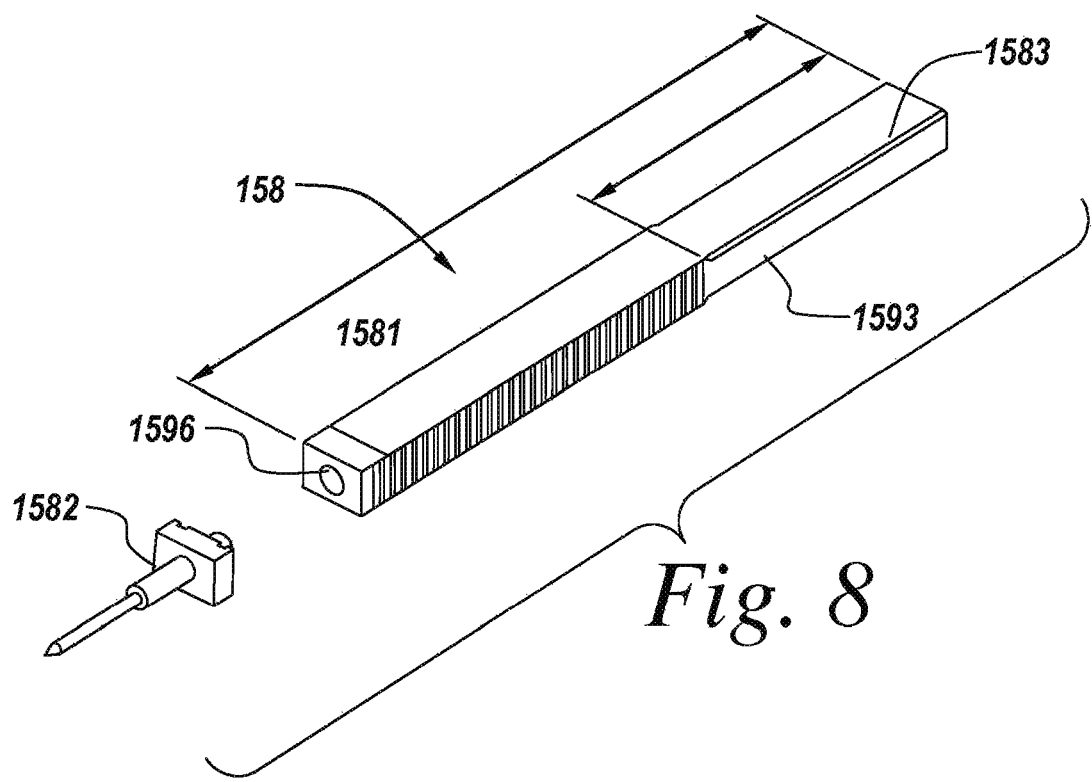
Fig. 8
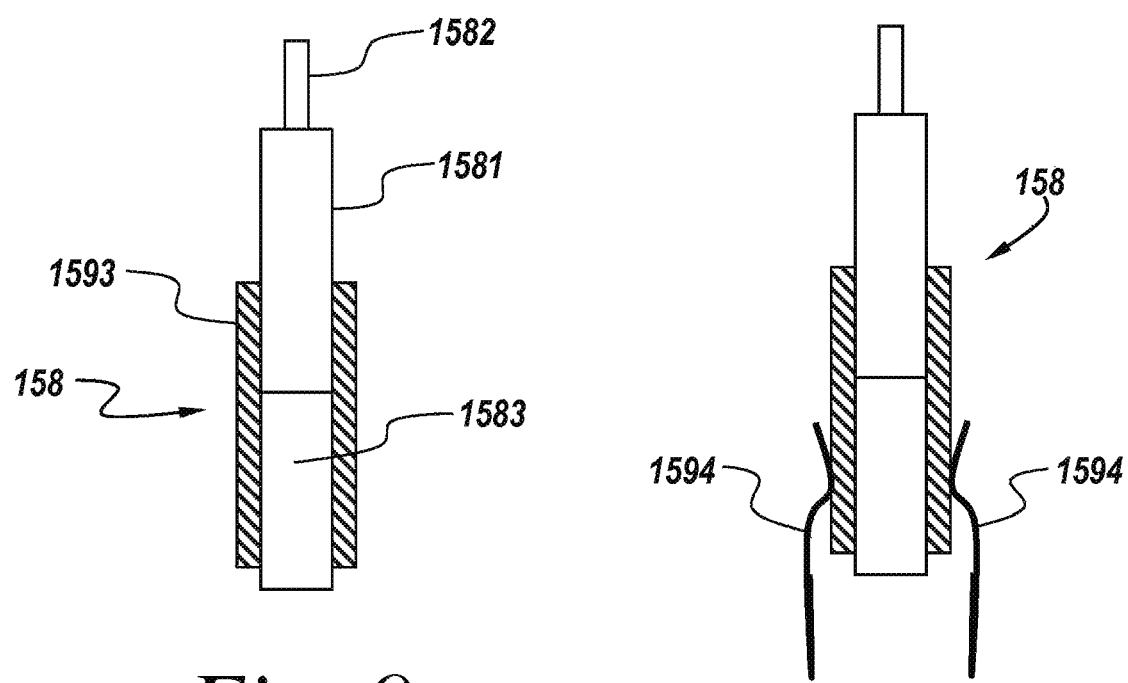
Fig. 9
Fig. 10

ACTUATION OF PARALLEL MICROFLUIDIC ARRAYS

RELATED APPLICATIONS

This application is a continuation of U.S. application Ser. No. 15/042,996, filed Feb. 12, 2016, which is a continuation of U.S. Ser. No. 14/517,396, filed Oct. 17, 2014 and now U.S. Pat. No. 9,260,693, which is a continuation-in-part of U.S. Ser. No. 13/371,277, filed Feb. 10, 2012 and now U.S. Pat. No. 8,863,962, which is a continuation of U.S. Ser. No. 11/800,469, filed May 4, 2007 and now U.S. Pat. No. 8,123,044, which claims priority to U.S. Provisional Ser. No. 60/798,154, filed May 5, 2006, and entitled "Actuation of Parallel Microfluidic Arrays." U.S. Ser. No. 14/517,396, filed Oct. 17, 2014 is also a continuation-in-part of U.S. Ser. No. 14/179,760, filed Feb. 13, 2014 and now U.S. Pat. No. 9,823,252, which is a continuation of U.S. Ser. No. 13/240,521, filed Sep. 22, 2011 and now U.S. Pat. No. 8,679,422, which is a continuation of U.S. Ser. No. 11/295,183, filed Dec. 5, 2005 and now U.S. Pat. No. 8,277,764, which claims priority to U.S. Provisional Ser. No. 60/633,396, filed Dec. 3, 2004, and entitled "Unitary Cartridge For Particle Processing". The contents of each application identified above is herein incorporated by reference in their entirety.

FIELD OF THE INVENTION

The present invention relates to an actuator for use in a microfluidic particle processing system or device. In particular, the present invention relates to an actuator for use with a parallel array microfluidic sorting device for sorting particles in a plurality of parallel channels.

BACKGROUND

Microfluidic devices may be used in a variety of applications to perform any number of microfluidic processes on particles.

In the fields of biotechnology, and especially cytology and drug screening, there is a need for high throughput sorting of particles. Examples of particles that require sorting are various types of cells, such as blood platelets, white blood cells, tumorous cells, embryonic cells and the like. These particles are especially of interest in the field of cytology. Other particles are (macro) molecular species such as proteins, enzymes and poly-nucleotides. This family of particles is of particular interest in the field of drug screening during the development of new drugs.

Methods and apparatuses for particle sorting are known, and the majority described in the prior art work in the condition where the particles are suspended in a liquid flowing through a channel network having at least a branch point downstream and are operated according the detect-decide-deflect principle. The moving particle is first analyzed for a specific characteristic, such as optical absorption, fluorescent intensity, size, or another suitable characteristic. Depending on the outcome of this detection phase, it is decided how the particle will be further handled. The outcome of the decision is then applied to deflect the direction of specific particle towards a predetermined branch of the channel network.

Of importance is the throughput of the sorting apparatus, i.e. how many particles can be sorted per unit of time. Typical sorting rates for sorters employing flows of particle suspension in closed channels are in the range from a few hundred particles per second to thousands of particles per second, for a single sorting unit.

In certain microfluidic processes, such as particle sorting, certain actuators used to actuate a process, such as separation of particles having a predetermined characteristic from particles that do not have a predetermined characteristic, may present drawbacks. For example, certain actuators may take up a relatively large amount of space on a microfluidic chip, limiting the efficiency with which actuators can be packaged on the microfluidic chip, thereby also limiting the density or efficiency of packing of an array of parallel channels.

SUMMARY

The present invention provides an improved actuator for use in a microfluidic particle sorting system. In one embodiment, the present invention provides a staggered packing scheme for a plurality of actuators used to selectively deflect a particle in an associated sorting channel from a stream of channels. In another embodiment, an actuator block is provided for housing a two-dimensional array of actuators, each configured to align with an actuation port in an associated sorting chip containing a plurality of sorting channels. The actuator block may include a built-in stressing means to pre-stress each actuator housed by the block. In another embodiment, an actuator comprising a piezo-electric stack may employ contact-based electrical connection rather than soldered wires to improve packing density. In one embodiment, the actuator is an external actuator. That is, the external actuator is external to the substrate in which the sorting channels are formed.

According to one aspect of the invention, a system for sorting particles, comprises a microfluidic chip containing a plurality of microsorters, each microsorter having an actuation port for interfacing with a displacement actuator for selectively actuating the microsorter to deflect a particle having a predetermined characteristic from a stream of particles, wherein at least one of the actuation ports of a first microsorter is located in a different coordinate along the chip from an actuation port of a second microsorter and a block holding a plurality of displacement actuators such that the location of each actuator in the block corresponds to the location of an associated actuator ports in the microsorter chip when the block and chip are brought together.

According to another aspect of the invention, a system for providing dense arrays of displacement actuators comprises a block assembly that holds actuators for selectively activating an associated sorter in a fixed two-dimensional array, a layer in the block assembly which compresses each actuator against an independent flexing means to provide pre-stress and a plurality of actuation pins mounted in the block.

According to still another aspect of the invention, a displacement actuator device comprises a piezoelectric stack, an actuating pin for contact with a surface to be displaced connected to a first end of the piezoelectric stack, a mounting-pin for holding the mounting the displacement actuator device coupled to a second end of the piezoelectric stack and a conductive coating disposed over the mounting-pin and extending at least partially over the piezoelectric stack to provide an electrical connection to the piezoelectric stack.

BRIEF DESCRIPTION OF THE FIGURES

FIGS. 5a-5d illustrate another embodiment of the particle sorting module during sorting of a stream of particles based on a predetermined characteristic.

FIG. 8 illustrates an embodiment of an actuator used to selectively actuate a sorting switch in the particle sorting system of FIG. 1.

FIG. 9 illustrates another embodiment of the actuator.

FIG. 10 illustrates the actuator of FIG. 9 including contact springs to provide an electrical connection to the actuator.

DETAILED DESCRIPTION

The present invention provides an improved actuation system for use in a microfluidic particle sorting system that sorts particles suspended in a liquid. The particle sorting system provides high-throughput, low error sorting of particles based on a predetermined characteristic. The present invention will be described below relative to illustrative embodiments. Those skilled in the art will appreciate that the present invention may be implemented in a number of different applications and embodiments and is not specifically limited in its application to the particular embodiments depicted herein.

Figure 1:
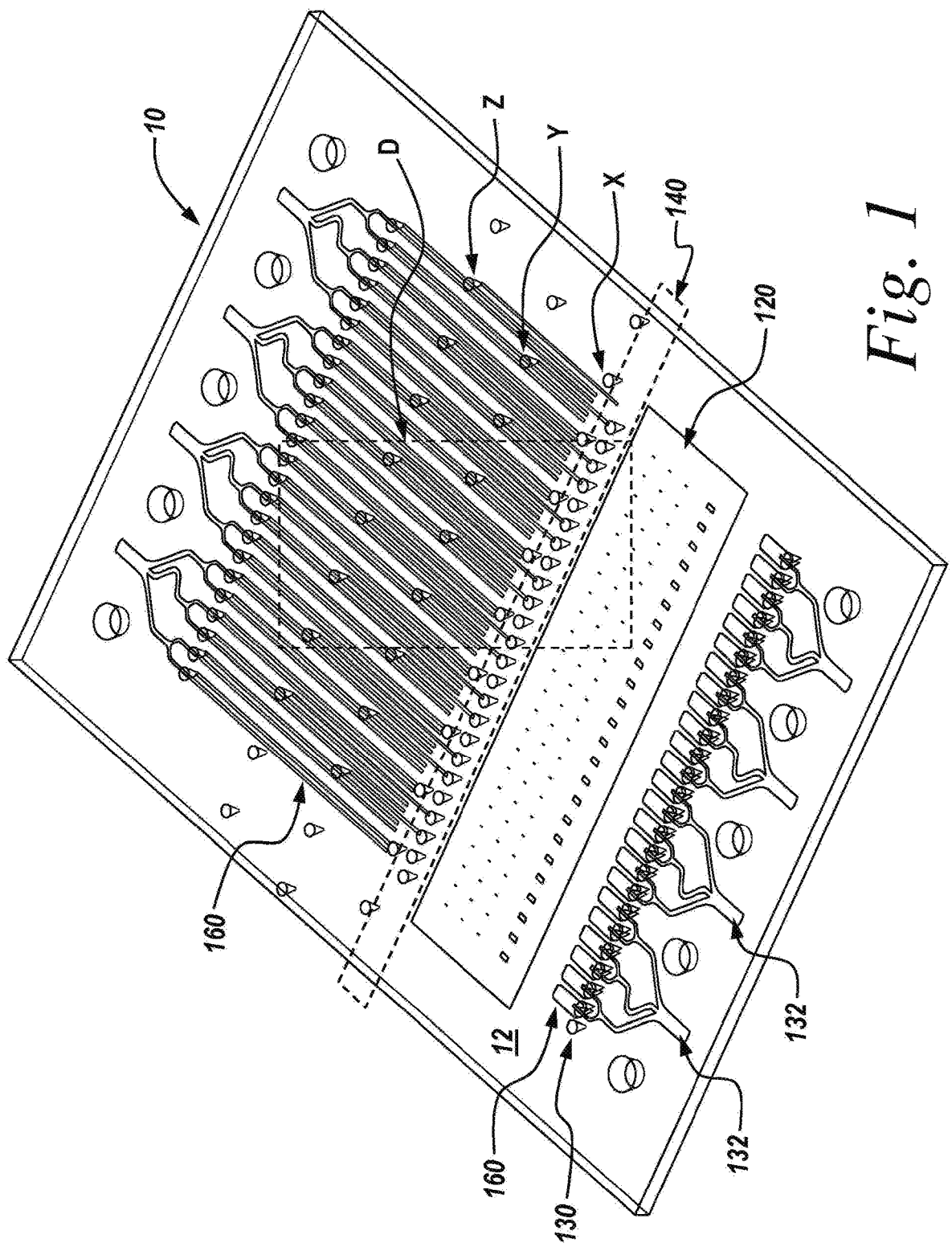
FIG. 1 illustrates a microfluidic particle sorting system according to an illustrative embodiment of the invention.

FIG. 1 illustrates a microfluidic particle processing system 10 according to an illustrative embodiment of the invention. The illustrative particle processing system comprises a particle sorting system for sorting particles flowing through a plurality of parallel channels based on one or more predetermined characteristics. The illustrative particle processing system 10 is formed on a substrate 12 and includes a number of processing channels, illustrated as sorting channels 160, for processing streams of an input sample in parallel. The processing system 10 includes a plurality of sample inlets 130 for inputting a sample to the system. In the illustrative embodiment, the sample inlets 130 intersect inlet channels 132, which flow a processing fluid, such as sheath fluid through the system. The sample inlets 130 and inlet channels 132 create a sheath flow carrying particles to be processed by the system through the parallel processing channels 160.

A suitable sheath flow system is described in U.S. patent application Ser. No. 10/979,848, filed Nov. 1, 2004, the contents of which are herein incorporated by reference. However, the invention is not limited to such a manner of inputting a sample and/or sheath flow to a particle processing system, and any suitable means may be used.

A detection region 120 receives the sheath flow containing the particles to be processed flowing through the parallel channels 110 and analyzes the particles. In the illustrative embodiment, the detection system observes the particles to identify particles having a predetermined characteristic. The detection region includes one or a plurality of detectors for sensing a predetermined characteristic in a target particle flowing through the channels 160.

A suitable detection system for analyzing particles is described in U.S. patent application Ser. No. 10/915,016, the contents of which are herein incorporated by reference. One skilled in the art will recognize that any suitable means of analyzing particles may be used.

In a processing region 140, the processing system 10 performs a selected process on the particles flowing through the channels 110. In the illustrative embodiment, the processing region contains a series 150 of switches for separating particles determined by detectors in the detection region 120 to have one or more predetermined characteristics from particles not having the predetermined characteristic.

Figure 2:
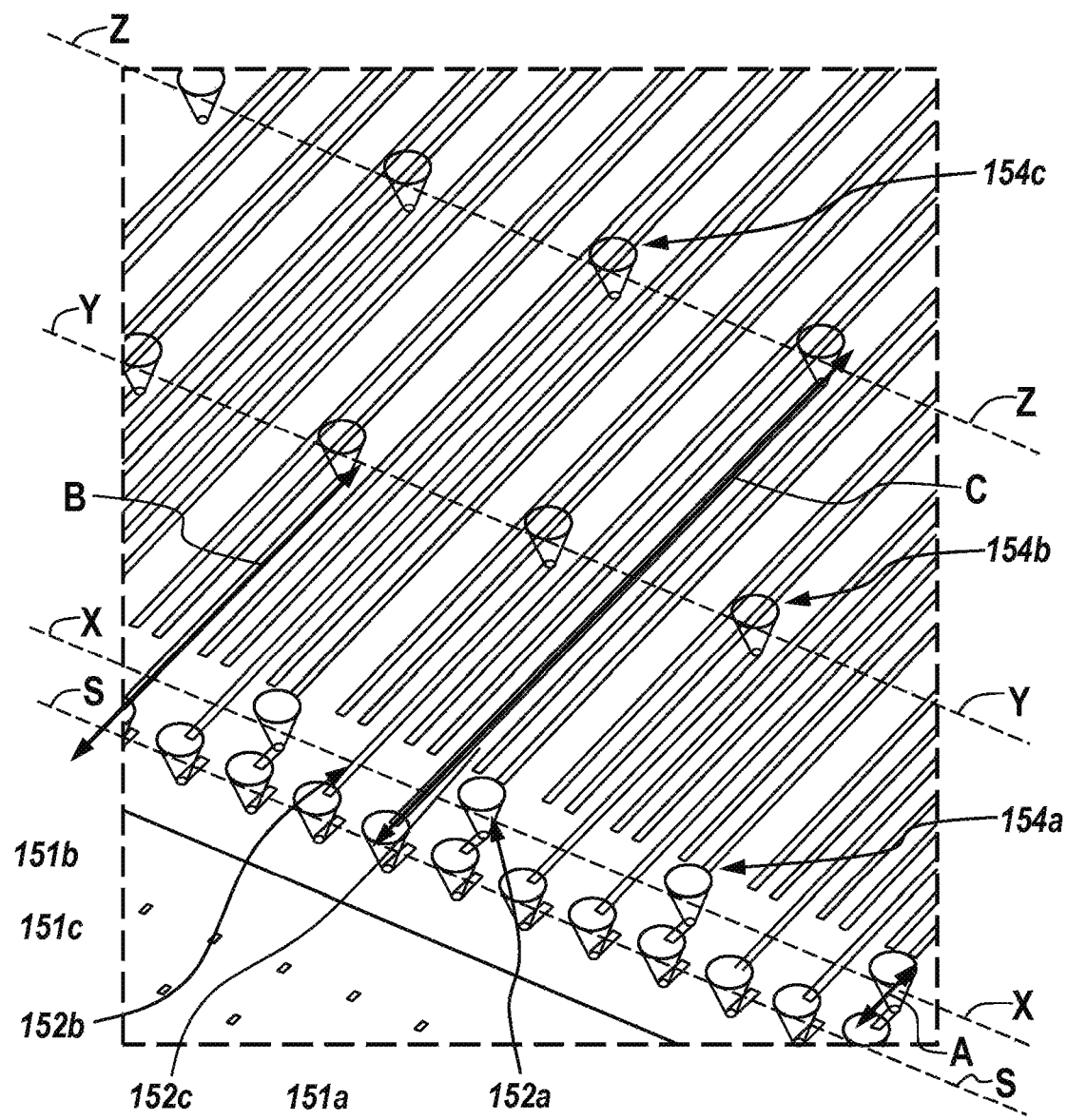
FIG. 2 is a detailed view of a region of the microfluidic particle sorting system of FIG. 1.

FIG. 2 is a detailed view of the region D in the particle processing system 10 of FIG. 1.

Figure 3:
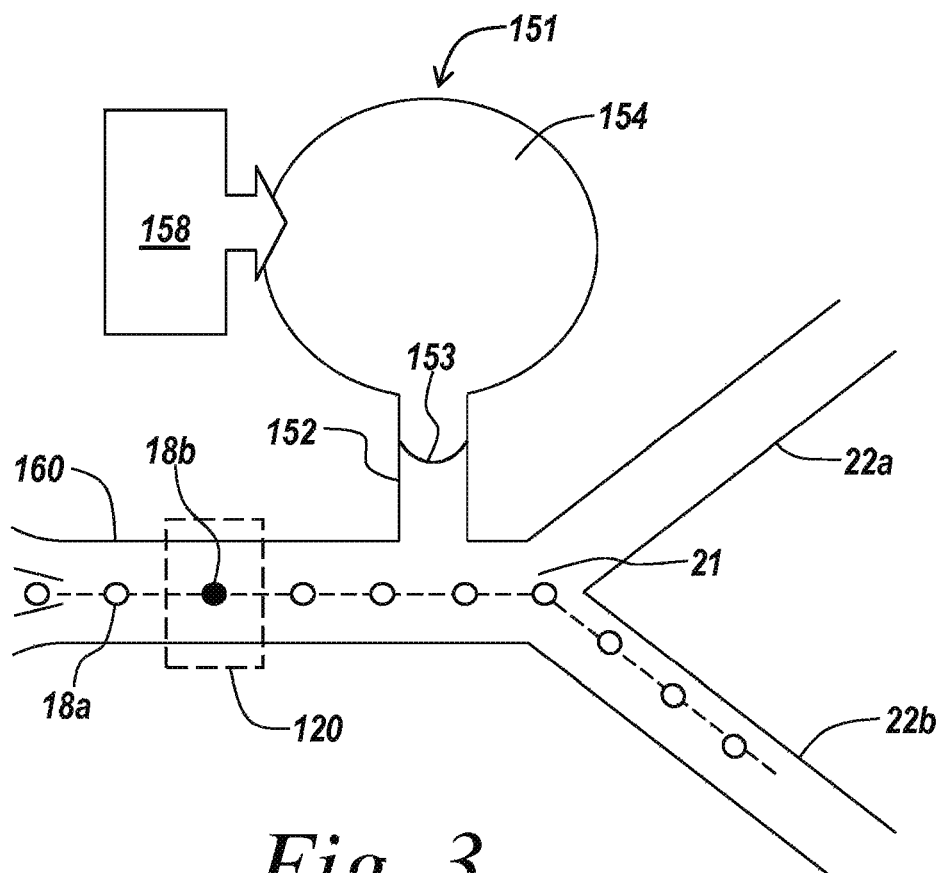
FIG. 3 illustrate a particle sorting module in the microfluidic particle sorting system according to one embodiment of the invention.

FIG. 3 illustrates a suitable switch 151 employed in the processing region of an illustrative embodiment of the invention. Each sorting channel 160 is associated with a dedicated switch 151 to perform sorting of particles within that channel. As shown, the sorting channel 160 conveys the particles suspended in the carrier liquid through the switching region. In the sorting region, the sorting channel 160 branches into a first branch 22a and a second branch 22b at a branch point 21. The illustrative switch 151 separates particles by selectively applying a pressure pulse to selected particles 18b in the channel 160 identified by the detection region 120 to deflect particles having the predetermined characteristic into a first outlet 22a of the channel, while particles 18a not having the predetermined characteristic flow into a second outlet 22b of the channel 160. The detection region 120 is defined in the sorting channel upstream of the switching region, and is associated with a detector, as described above, to sense a predetermined characteristic of particles in the detection region 20.

According to the illustrative embodiment, each switch 151 includes a side channel 152 intersecting the sorting channel 160 in the switching region. A fluid, such as the sheath fluid, partially fills the side channel 152 to form a meniscus 153 therein. The side channel 152 extends to and terminates in a sealed chamber 154, which is preferably filled with a fluid, such as air, other than the sheath fluid. The meniscus 153 interfaces and forms a barrier between the sheath fluid and the sealed chamber 154. The chamber 154 preferably includes a flexible or movable wall, which, when deflected or moved inwards, creates an increase in pressure in the sealed chamber 154. The chamber 154 serves as an actuation port to interface the sorting components formed on the substrate with an external actuator, as described below.

An actuator 158 is also provided for actuating the switch 151 when the detector in the detection region identifies a particle having a predetermined characteristic. In some embodiments, the actuator 158 is external to the switch 151. The actuator, when actuated, momentarily causes a flow disturbance in the sorting channel 160 to deflect the flow therein. The actuator 158 selectively increases the pressure in the chamber 154, causing the flow in the sorting channel near the side channel 152 to be displaced inwards, substantially perpendicular to the normal flow in the sorting channel 160. This transient liquid displacement, having a component perpendicular to the normal flow in the sorting, can be applied in deflecting particles having predetermined characteristics to separate them from the remaining particles in the mixture.

The actuator 158 is preferably a displacement actuator, as described below.

A buffer may optionally be provided for absorbing the pressure pulse created by the actuator.

Preferably, the actuator 158 is external to the substrate in which the sorting channels 160 are formed. The sealed chamber 154 may also be formed external to the substrate.

Figure 4:
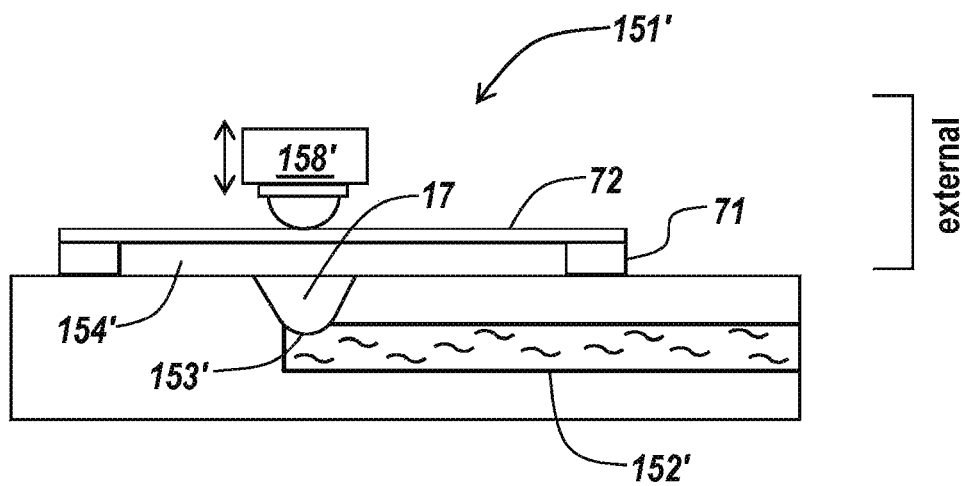
FIG. 4 illustrates another embodiment of a particle sorting module suitable for use in the particle sorting system of the invention.

FIG. 4 illustrates another embodiment of a switch suitable for creating a pressure pulse to separate particles of interest from other particles in a stream of particles and/or acting as a buffer for absorbing a pressure pulse according to the teachings of the present invention. As shown, the switch 151' is formed adjacent to a side passage 152' formed in a substrate 12 which leads to the sorting channel 160. The side passage 152' includes a fluid interface port 17 formed by an aperture in the side wall of the passage. A sealed compression chamber 154' is positioned adjacent to the side passage 152' and communicates with the side passage through the fluid interface port. The illustrative chamber 154' is formed by a seal 71 and a flexible membrane 72. The carrier fluid in the side passage 152' forms a meniscus 153' at the interface between the side passage and the chamber. The actuator 158' depresses the flexible membrane to increase the pressure in the chamber, which deflects the meniscus and causes a pressure pulse in the carrier fluid.

Figure 5A:
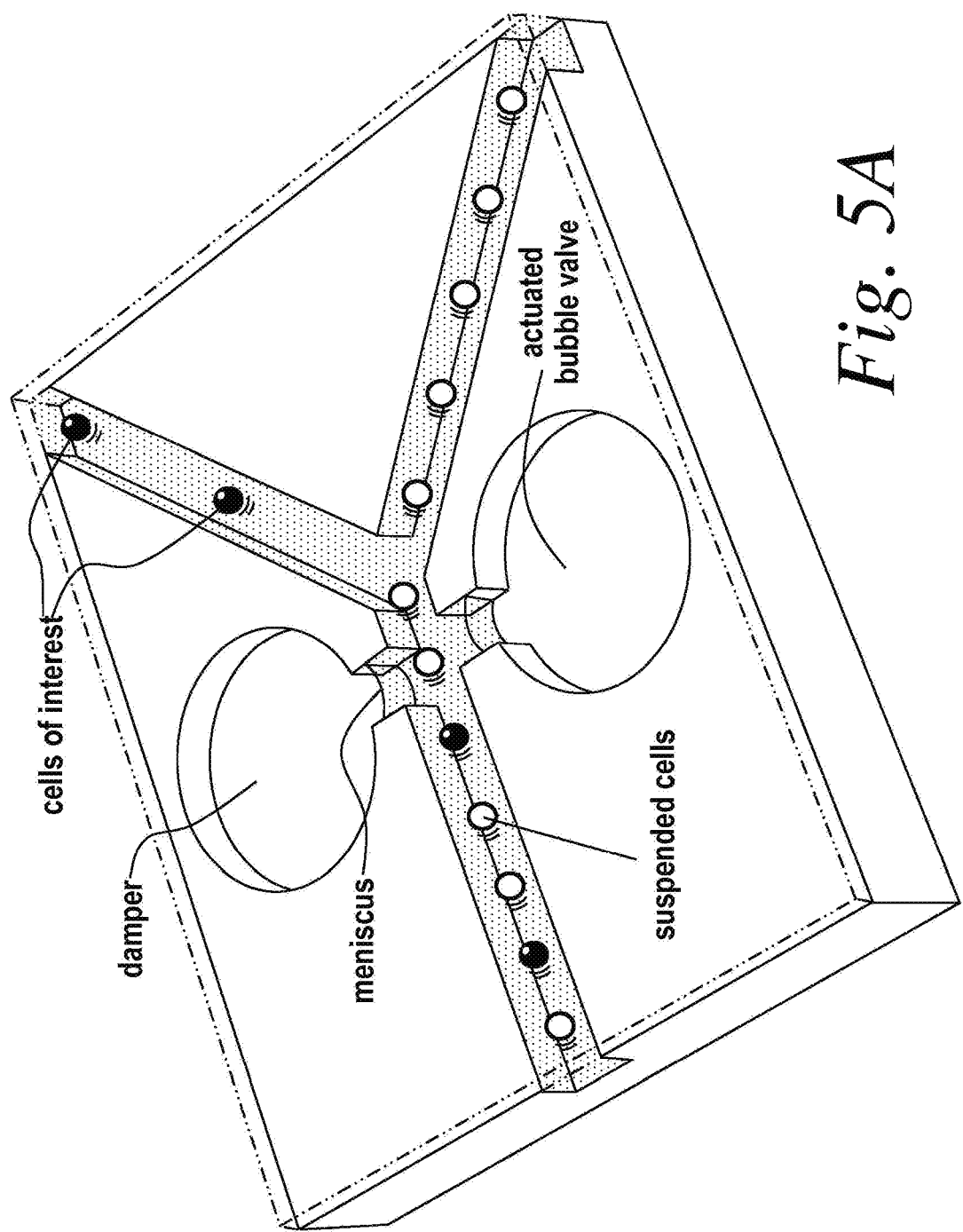

FIGS. 5a-5d illustrate the switching operation of switch 151 in the particle sorting system 10 of FIGS. 1-4. In the embodiment of FIGS. 5a-5d, the switch 151 includes a buffer for absorbing pressure pulses created when the actuator 158 increases the pressure in the chamber 154. The buffer includes a second side passage terminating in a sealed chamber 154' formed opposite the switch side passage 154. In FIG. 5A, a detector in the detection region 120 senses the predetermined characteristic in a particle and raises a signal to activate the actuator 158. Upon activation of the actuator, the pressure within the reservoir 154 of the switch 151 is increased, deflecting the meniscus 153 and causing a transient discharge of liquid from the first side passage 152, as indicated by the arrow in FIG. 5B. The sudden pressure increase caused at this point in the sorting channel causes liquid to flow into the second side passage forming the buffer, because of the resilient properties of the second reservoir buffer. This movement of liquid into the buffer side passage is indicated with an arrow. As a result, as can be seen in FIG. 5C, the flow through the sorting channel is deflected, causing the selected particle of interest 18b located between the first side passage 154 and the buffer side passage to be shifted perpendicular to its flow direction in the normal state. The deflected particle of interest, displaced radially by the pressure pulse, then flows into the first outlet channel 22a, while unselected particles, unaffected by the pressure pulse, flow into the second outlet channel 22b, thereby separating particles having the predetermined characteristic from particles not having the predetermined characteristic, as shown in FIGS. 5A and 5D.

When the actuator 158 is deactivated, the pressure inside the reservoirs 154, 154' returns to the normal pressure, allowing for normal flow of particles into the second outlet channel 22b.

This process of detecting and selective deflecting of particles may be repeated many times per second for sorting particles at a high rate. Adopting the fluid switching as described, switching operations may be executed up to around several thousand switching operations per second, yielding sorting rates in the order of million sorted particles per hour.

A suitable switching mechanism described in U.S. Pat. Nos. 6,877,528, 6,808,075, 6,976,590 and 7,157,274 and U.S. patent application Ser. No. 11/295,183 now U.S. Pat. No. 8,277,764, the contents of which are herein incorporated by reference.

According to an illustrative embodiment of the invention, as shown in FIGS. 1 and 2 the actuators 158 for the array of sorting channels 160 are staggered on the microfluidic substrate 12 to allow dense packing of the channels on the substrate 12. For example, in the illustrative embodiment, the switching regions of the switches, where the side channels 152 intersect the sorting channels 160 in each switch, may be spaced substantially equally in region 140. The side channels 152 of the switches may have varying lengths to allow the location of the actuators 158 at the end of the side channels 152 to be staggered. Nevertheless in other embodiments of the present invention, the switches in the switching region can be staggered. Staggering the switches requires compensation for different times from detection to actuation (for each length) and possibly compensation for flow resistance matching to allow for the fact that the resistance in the sorted and unsorted channels (the y-channels post switching joint) would not all be intrinsically matched.

In the illustrative embodiment, the actuators 158 are staggered at different coordinates along the substrate in intervals of three. As used herein, the term "coordinate" refers to a longitudinal position of an element along a substrate. For example, the term coordinate may refer to the distance of an actuator and/or actuator port from a row of switches, or another row parallel to a front (input) end or back (output) end of the substrate. In this embodiment the actuation ports are staggered on chip by using asymmetric actuator port arm lengths while leaving the location of the switching joints in a line S. For example, the actuators 158 may be staggered by selectively extending the side channels of the switches to locate the actuator port and chamber 154 at staggered distances from the switching region. For example, in the illustrative embodiment shown in FIGS. 1 and 2, the channels are groups in subsets of threes. A first side channel 152a of a first switch 151a in a series of three switches has a first length A, terminating in a sealed chamber 154a forming an actuator port at line X, such that the corresponding actuator is located along line X. A second side channel 152b of a second switch 151b has a second length B, terminating in a sealed chamber 154b forming an actuator port at line Y, such that the corresponding actuator is located along line Y. A third side channel 152c of a third switch 151c has a third length C, terminating in a sealed chamber 154c forming an actuator port at line Z, such that the corresponding actuator is located along line Z, which is furthest from the switching regions, which are aligned along line S. Thus, every third actuator and associated chamber aligns along the same coordinate of the substrate (i.e., the same row). In this manner, one third of the actuators for the series of sorting channels and switches are located along line X, closest to switching line S, a second third of the actuators are located along line Y, farther from the switching line S, and the last third of the actuators are located along line Z, farthest from the switching line S.

The illustrative packing scheme thus enables dense packing of the sorting channels. In one embodiment, the sorting channels may be packed with a spacing between channels at as little as 900 microns. In contrast, were the actuators to align along the same line, more space would be required.

By using staggering actuation ports in every third channels the illustrative embodiment of the invention enables conventional piezo stacks or electroconstrictive or other type of displacement actuator that are generally too large to pack linearly.

Although the array of actuators and the corresponding actuation ports of the microfluidic particle processing system are illustrated with three staggered rows, those skilled in the art will appreciate that the array of actuators and the corresponding actuation ports of the microfluidic particle processing system of the present invention can have fewer rows, for example, two rows, or more than three rows, for example, four rows, five rows, six rows and so on.

Alternatively, the switching points in region 140 may also or alternatively be staggered, so that line S comprises several staggered lines.

In this embodiment, the actuator array and the actuator port array are designed to match spacing and reach a new minimum interchannel spacing.

Figure 6:
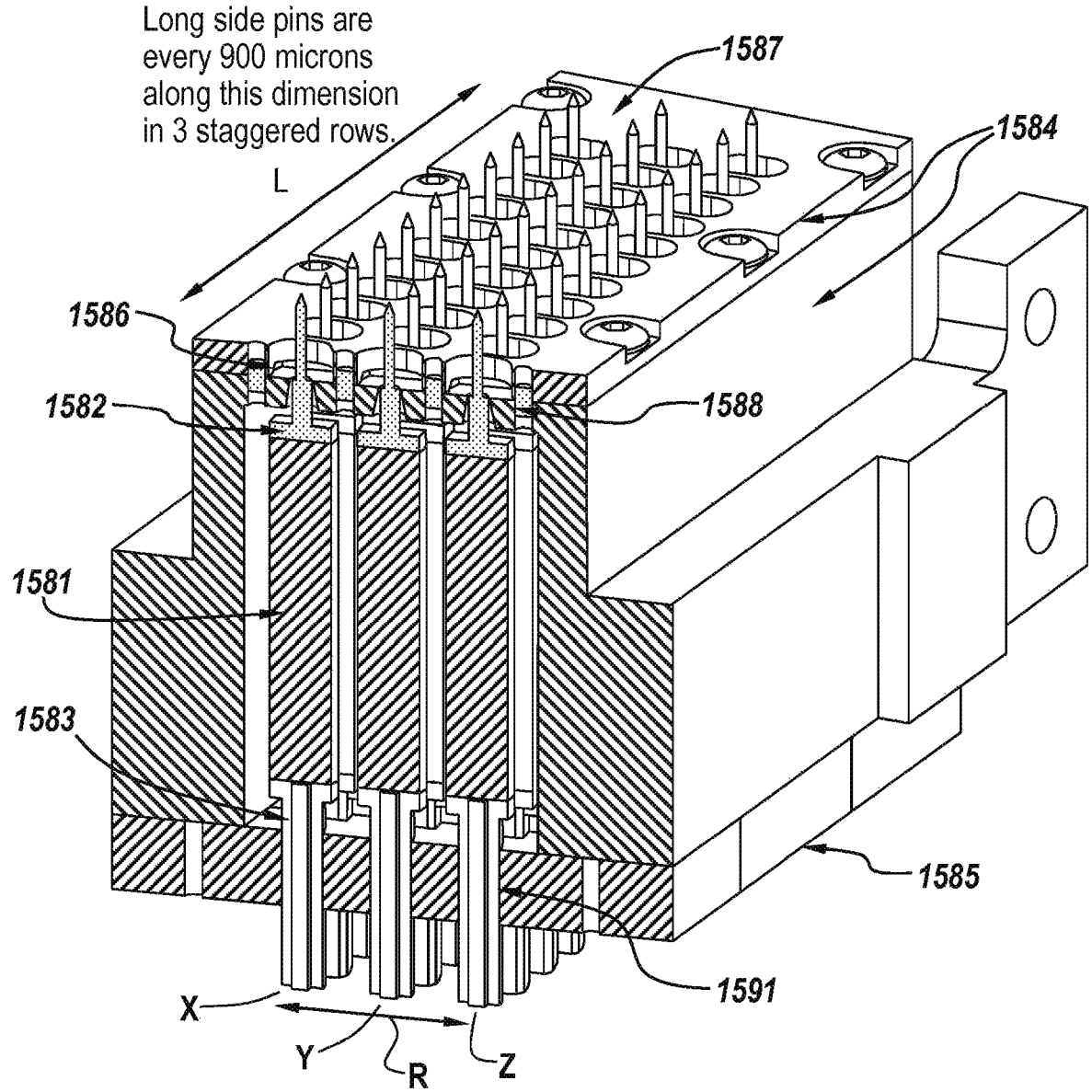
FIG. 6 illustrates an embodiment of an actuator block for housing a plurality of external actuators used with the particle sorting system of FIG. 1 in a two-dimensional array.

According to another embodiment of the invention, the particle processing system may include a self-aligning actuator packing block containing a plurality of actuators for actuating a plurality of switches in the particle processing system. FIG. 6 illustrates an embodiment of a self-aligning actuator packing block 400 suitable for actuating switches when a detection system 120 detects a predetermined characteristic in a particle in a sorting channel 160. When coupled to the substrate 12, each actuator 158 in the block aligns with a sealed chamber at the termination of a switching side channel to associate the actuator with a selected switch and sorting channel 160. A controller selectively actuates the appropriate actuator 158 in the block when signaled by the detection system 120 to increase pressure in an associated switching chamber, causing deflecting of a meniscus in an associated switching side channel to deflect a targeted particle in the associated sorting channel. The actuator block 400 may actuate one, a plurality or all of the actuators at once, if appropriate.

The illustrative actuators include built-in pre-stressed springs, flexures or other suitable flexible devices for each actuator, such as for each actuator pin.

In the illustrative embodiment, a plurality of actuators 158 are densely packed in a two-dimensional array. Each illustrative actuator 158 includes a piezoelectric stack 1581, or other suitable displacement actuator that expands or retracts when supplied with a particular signal. Alternatively, the piezoelectric stack may comprise an electroconstrictive displacement actuator known in the art. An actuation pin 1582, or other suitable device, is mounted through any suitable means to the front side of the piezoelectric stack. The actuation pin 1582 may be mounted to the piezoelectric stack through any suitable means, including glue, cement or other bonding means. A mounting pin 1583 is mounted on the back of each piezoelectric stack 1581. The actuation pin 1582 is configured to extend from the block 400 and contact a movable wall of a sealed switching chamber when the piezoelectric stack expands to create the necessary pressure pulse to selectively deflect a targeted particle in an associated sorting channel. Together, the stacked actuation pin 1582, piezo stack 1581 and mounting pin 1583 forms a "piezo pin" unit.

The block for housing the array of piezo pins includes a back plate 1585, into which the piezo pins may be fixed. The piezo pins are preferably fixed to the back plate 1585, such that the mounting pins 1583 extend through apertures 1591 formed in the back plate. The mounting pins 1583 may conduct electricity from a source to actuate the actuator. After fixing the piezo pins, the back plate is then mounted into a front block 1584 so that the piezo pins are compressed against flexures 1586 located in the top 1587 of the front block 1584. Any suitable device may be used to provide compression of the piezo pins and the invention is not limited to the illustrative flexures 1586. The top 1587 of the front block 1584 faces the substrate 12 of the sorting system when the block is coupled to the substrate. The tips of the piezo pins, formed by the actuation pins 1582, protrude through apertures 1588 in the front block so that they may contact the actuation ports of the microsorter system without mechanical interference between the substrate 12 and the actuator block system 400.

In the illustrative embodiment, the actuator block 400 include three rows of piezo pins, shown along axis R. Each row corresponds to one of the lines X, Y and Z along which the sealed chambers at the termination of the side channels for each switch in the array of switches on the substrate are formed. In each row, the actuators are spaced along the length L of the actuator block so as to align with each sealed chamber in the subset of switches disposed along the associated line X, Y or Z. While the illustrative embodiment shows a staggering at intervals of three, one skilled in the art will recognize that the actuator side channels and associated actuators may be staggered at any suitable interval. For example, for alternate staggering, two rows of actuators would be formed in the block. The number of rows in the actuator block corresponds to the number of subsets of switches in which the staggering occurs.

The illustrative actuator block 400 implements implement a dense packing array to conserve space. In the illustrative embodiment, each actuator, i.e., piezo pin, or other suitable displacement actuator, is spaced at less than about 4 mm spacing between actuator centers, such that the actuation pins are found linearly at less than 2 mm intervals along the long side of the block and preferably less than 1 mm.

In the illustrative embodiment, the flexures 1586 are provided to maintain the actuators in a pre-stressed state to promote reliable piezoelectric stack operation over long times and many cycles. In the resting position (zero voltage applied in one embodiment) the piezo pins or other actuation devices are held in compression. When a voltage is applied to the mounting pin, the mounting pin 1583 transmits the voltage to the piezoelectric stack 1581 to expand the actuator against the compressive pressure, thereby actuating the associated switch 151.

Figure 7:
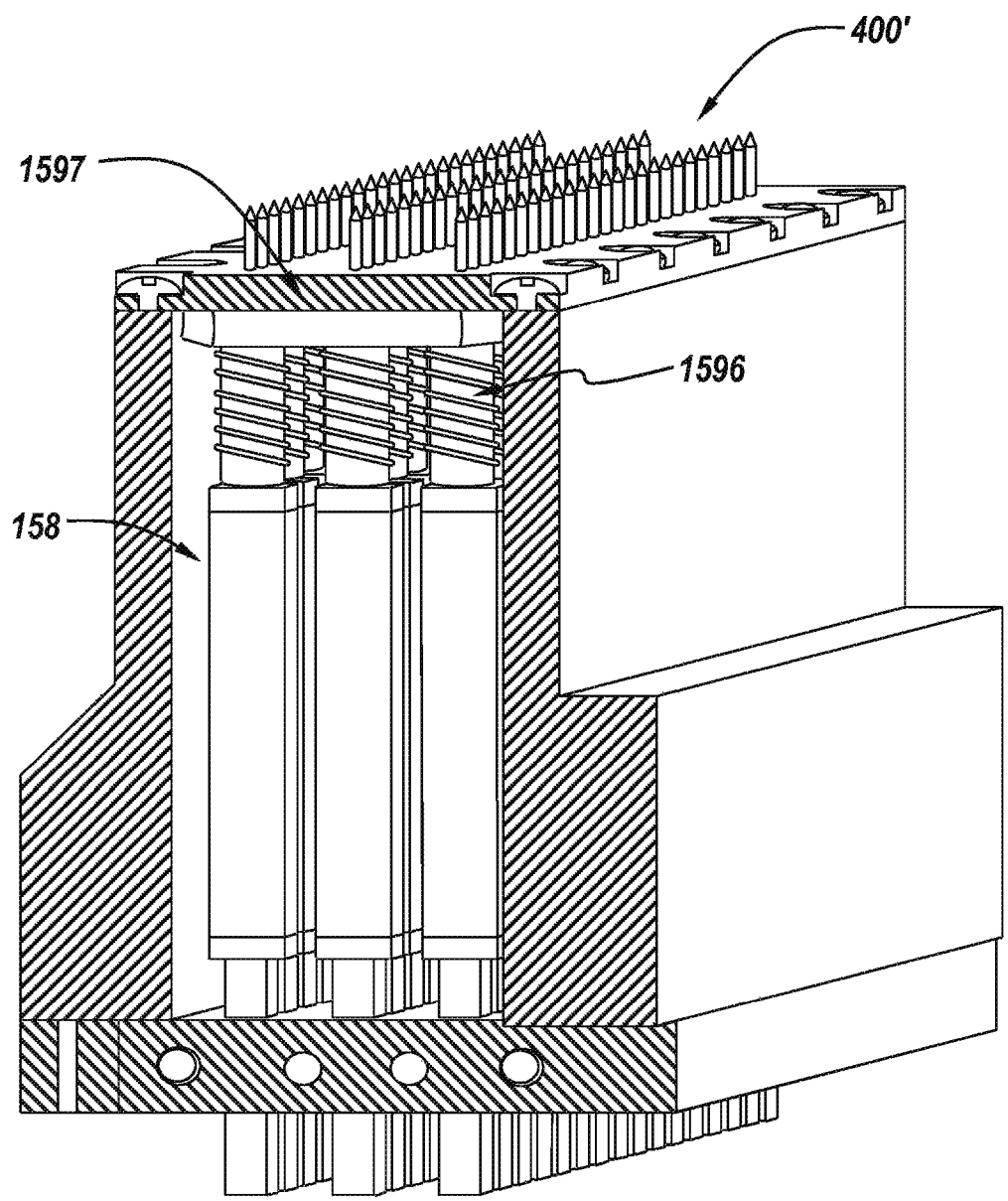
FIG. 7 illustrates another embodiment of the actuator block.
Figure 11A:
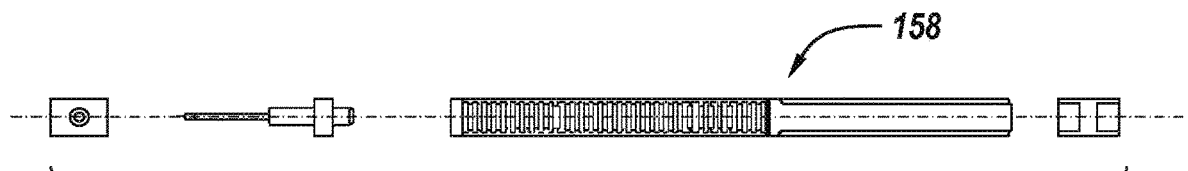
FIGS. 11A-11D illustrate the actuator of FIG. 8.
Figure 11B:
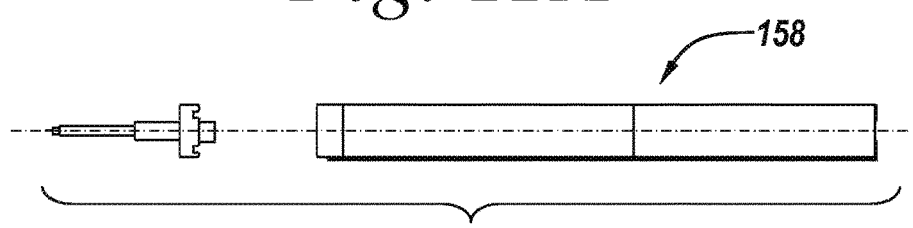
Figure 11C:
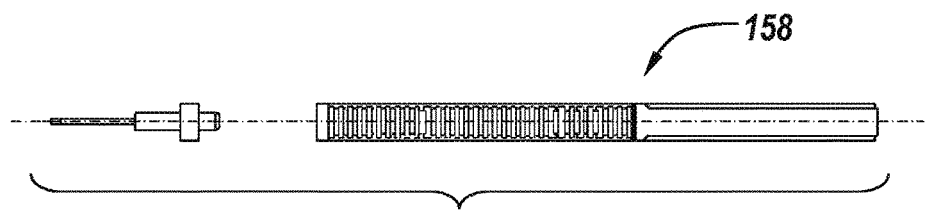
Figure 11D:
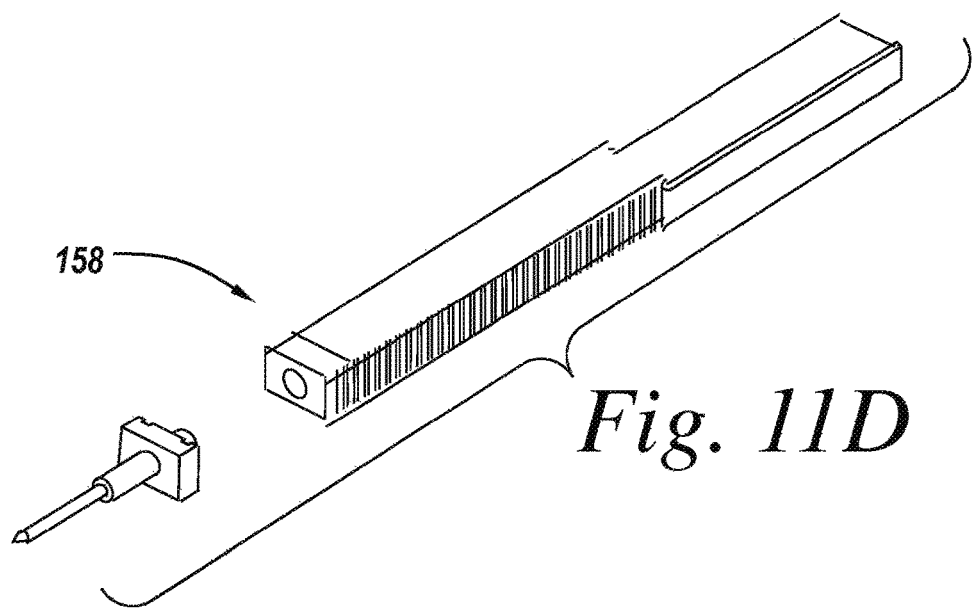

According to another embodiment of the invention, shown in FIG. 7, an actuator block 400' for a particle processing system may employ helical springs 1596 to compress the displacement actuation device, such as a piezo pin, in a resting position to provide built-in pre-stress. A helical spring 1596 may be placed over each piezo pin 158 or other actuation device. The spring loaded piezo pins may then be compressed all together against a rigid surface 1597, which is located in the top of the actuator block 400' in the illustrative embodiment. The rigid surface 1597 may be located in any suitable location.

Referring to FIGS. 8-11*d*, the present invention may also or alternatively provide enhanced performance by providing the piezo-pin actuator with a contact based electrical connection, rather than employing soldered or crimped wires, thereby further improving packing density.

Piezo-stacks conventionally have wires soldered to the electrodes on opposite sides of the stack. In any dense packing implementation those wires would have to be brought out of the block and connected one at a time to the piezo driver electronics. In the illustrative electronic pin 158, the sides of the mounting pin 1583 at the back of the piezo-pin structure are coated with a coating 1593 (or metallized or have conductors mounted) with conducting material, such as metal, for example copper, which is extended over the sides of the piezo stack 1581 itself to allow the designer to use conductive springs 1594 mounted in or below the actuator block back plate to make electrical connection by insertion, similar to a integrated circuit chip in-line package pin socket.

The integrated conductor surfaces on the illustrative piezo stack based pins (piezo-pins) enable electrical connections to be made using conductive springs—enabling insertion connections instead of soldered ones.

As shown in FIG. 8, the actuation pin 1582 may be mounted to the piezo stack 1581 using a protrusion on the back end of the actuation pin that is received by a recess 1598 in the front end of the piezo stack 1581. Any suitable mounting means may be used.

Figure 12:
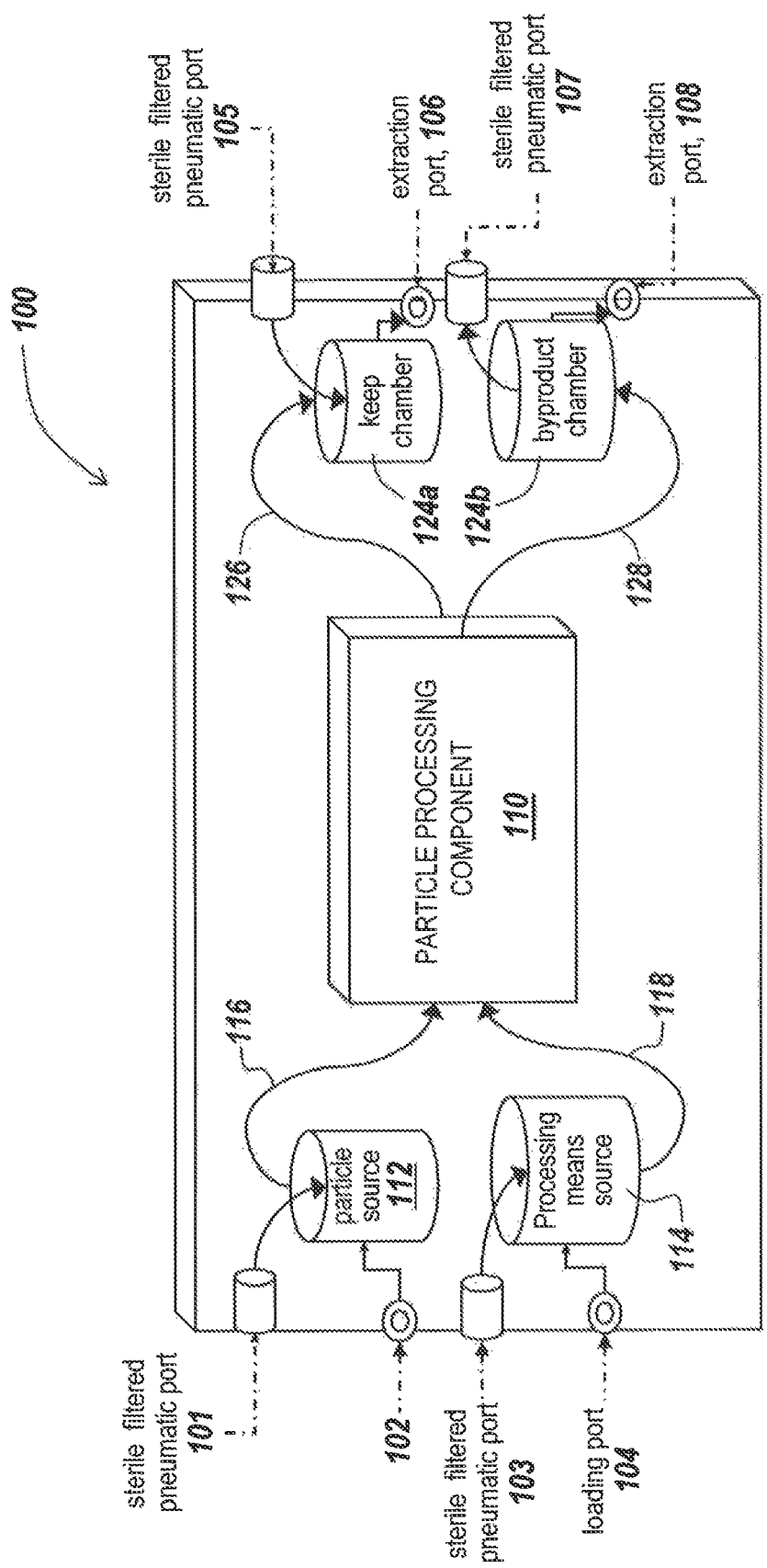
FIG. 12 illustrates a unitary cartridge for particle processing according to an Illustrative embodiment of the invention.

FIG. 12 illustrates a particle processing cartridge 100 for performing a process on a sample, having many, and preferably all, fluid contact surfaces encapsulated according to an illustrative embodiment of the invention. The illustrative unitary particle processing cartridge 100 can be designed to perform any suitable process or multiple processes on a sample. Preferably, the unitary particle processing cartridge performs a microfluidic process on a sample. The cartridge may contain one or more particle processing subsystems 110 enabling one or more unit processes to be applied to a sample, such as a suspension, loaded into the cartridge 100. The particle processing subsystem 110 may be separately inserted into and removable from the cartridge 100, or may be integrally formed on the cartridge substrate. For example, the cartridge substrate may have formed therein a recess or chamber for receiving the particle processing subsystem 110. Some examples of unit processes that may be incorporated into a unitary cartridge 100 include, but are not limited to, incubation or staining of particles, washing of particles, including variants where supernatant is purified, heating or cooling of particles in a suspension, mixing cells or other particles with chemicals or heads, size-based filtering of particles, depletion or enhancement of a subset of particles in the suspension, sorting of particles, and other suitable processes known in the art.

Ideally, in order to prepare particles, such as cells for research or clinical applications, using a unitary cartridge 100 of the illustrative embodiment of the invention, a user loads the "source", such as a cell suspension, into the cartridge via a sample input port 102, operates the cartridge using the processing subsystem 110 and extracts the final product in as finished a condition as possible via a processed sample output port 106. If a processing means, such as a sheath fluid, solution, mixing suspension, magnetic beads and so on, is necessary, the processing means may be loaded into the cartridge 100 via a processor input port. 104 and stored in a processing means source 114. Alternatively, a single port can serve as both the sample input port and the processor input port. An extraction port 108 may be used to access byproducts of the processing subsystem 110.

A plurality of chambers disposed between the ports and the subsystem 110 may also be provided. Preferably, at least some of the chambers are rigidly connected to each other to form the unitary cartridge 100. As shown, the illustrative cartridge 110 includes a sample input chamber 112 for storing a sample to be processed, which may be provided by the sample input port 102. The sample input chamber 112 is in fluid communication with the processing subsystem 110 via a fluid path 116. A processing means input chamber 114 may store a processing means provided via processor input port 104. A fluid path 118 fluidly connects the processing means input chamber 112 to the particle processing component 110. A processed sample chamber, illustrated as "keep" chamber 124a, stores a sample processed by the processing subsystem 110, and may be fluidly connected to the particle processing component 110 via a fluid path 126. A sample output port, such as extraction port 106 may be used to retrieve the sample from the processed sample chamber. A byproduct output chamber, illustrated as a "keep" chamber 124b, may store a byproduct of the process performed using the subsystem, such as unselected particles in a sorting system, or a byproduct solution for another process, which may be provided to the byproduct output chamber 124b from the particle processing component 110 using another fluid path 128. A plurality of pneumatic ports 101, 103, 105 and 107 in communication with the fluid paths applies pressure to facilitate fluid flow through the cartridge. In addition, a plurality of additional ports, chambers and fluid paths may be provided in the cartridge, depending on the type of process performed.

The unitary particle processing cartridge 100 may include a plurality of sample processing subsystems 110 in the cartridge. For example, two or more sample processing subsystems 110 may be disposed in series on the cartridge to allow sequential processing of a sample. An enrichment region between the serial processing subsystems may allow for resetting of sample parameters between processes. An example of a suitable enrichment region between two sample processing stages 110 is found in U.S. application Ser. No. 10/329,008. For example, the enrichment region may be formed by a filter disposed between the sample processing subsystems on the cartridge.

Figure 13:
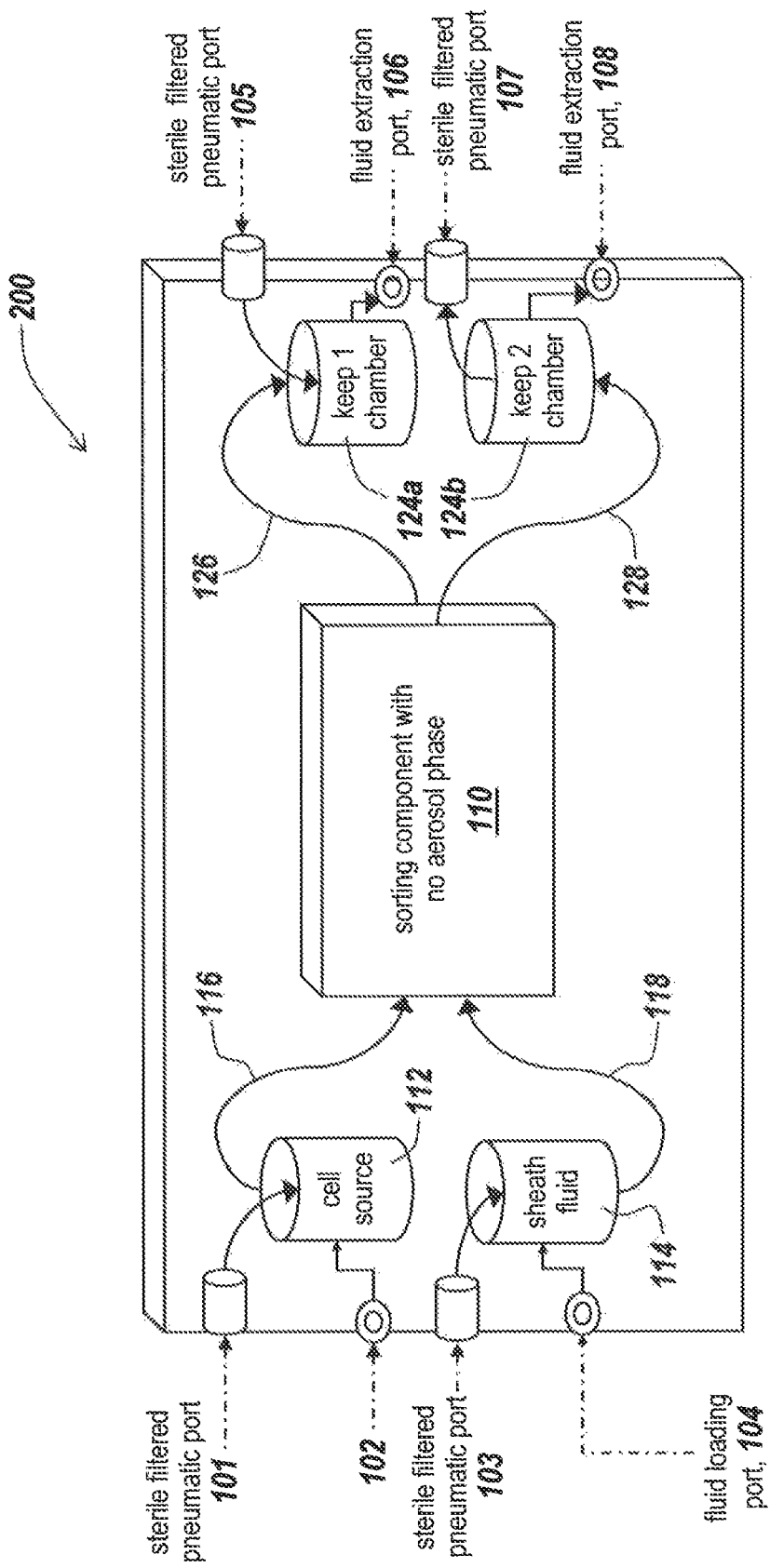
FIG. 13 illustrates a unitary cartridge for particle sorting according to an illustrative embodiment of the invention.

According to another embodiment, a unitary particle processing cartridge may be used for particle sorting. The illustrative cartridge 200 performs cell sorting, though one skilled in the art will recognize that the cartridge 200 may perform sorting on any type of particle.—FIG. 13 illustrates a unitary particle sorting cartridge 200 including a microfluidic based sorting component 120 for sorting particles without an aerosol phase according to an illustrative embodiment of the invention. Upstream of the soiling component 120, the cartridge 200 includes a cell source 112 for storing particles to be sorted, a sheath fluid source 114 storing a sheath fluid for facilitating a sorting process, a sterile filtered pneumatic port 101 for the cell source, a sample loading port 102 for the cell source, a sterile filtered pneumatic port 103 for the sheath fluid and a fluid loading port 104 for the sheath fluid reservoir 114. The pneumatic ports 101, 103 apply pressure to induce or facilitate fluid flow through the cartridge. Channels, illustrated as tubes 116 and 118, connect the cell source 112 and sheath fluid reservoir 114, respectively, to inlets of the soiling component 120. Downstream of the sorting component 120, the cartridge includes keep chambers 124a, 124 for collecting sorted particles, tubes 126, 128 connecting the outlets of the sorting component 120 to the keep chambers 124a, 124b. The cartridge also includes an extraction port 106, 108 for each keep chamber 124a, 124b, respectively, for extracting collected fluid from each keep chamber, and sterile fluid pneumatic ports 105, 107, respectively. The cartridge processes relatively large volumes (0.1 ml to 5000 ml of suspension) and equal or larger volumes of sheath fluid through the system and out into output chambers 124a, 124b.

The sorting component 120 may be separately manufactured, stored, and/or shipped, and subsequently inserted into the cartridge substrate 200, creating a flexible connection. Alternatively, the sorting component 120 may be integrally and rigidly formed on the cartridge substrate 200.

As shown, fluidic connections from the cell source 112 or sheath reservoir 114 to the sorting component 120 and from the sorting component to the keep chambers 124a, 124b, can be made with single tubes or arrays of tubes. The tubes creating the fluid paths can be of any appropriate diameter.

An embodiment of a unitary particle processing cartridge of the present invention, such as the unitary particle processing cartridge 100 shown in FIG. 12 or the unitary particle sorting cartridge 200 of FIG. 13 has several properties that are improvements in operation of a cell or particle sorting system. For example, most, and preferably all, of the fluid contact surfaces are built into one object ("the cartridge"). The unitary cartridge including all the fluid contact surfaces can be inserted into a processing instrument (the platform containing sorting optics, electronics, control software and other subsystems the suspension never contacts) with a single operation. The unitary cartridge can also be disposed of in a single operation after use. The cartridge can be sterilized after assembly all at once. The cartridge can be shipped to the user in a sterile, ready to use form. Each cartridge (and therefore all fluid contact surfaces needed for a single processing nm) can be given a barcode or other unique identification, making of the parts that represent possible sources of product contamination fully traceable. In addition, no fluid waste needs to be removed from the cartridge in operation. Rather, fluid waste can be disposed of with the disposal of the cartridge, without requiring separate handling of the fluid waste.

Use of a unitary particle processing cartridge of the present invention can enhance operator and product isolation. To use the cartridge to perform a particle processing operation, such as particle sorting, a user can receive the cartridge sealed and sterile from the manufacturer. The user may then take a cartridge to a biosafety hood, such as a sterile laminar flow hood, and perform a sterile operation (in the manner of conventional tissue culture for that type of sample) to load cell sample and sheath reservoirs. The cartridge is preferably sealed before and after this operation. The user places the cartridge in the sorting to instrument platform. The system soils the cells or particles in the sample into one or more of the keep chambers in the cartridge. The user removes the cartridge from the system and takes the cartridge back to the biosafety hood to remove the processed samples through their extraction ports. The user may then dispose of the used cartridge and unneeded fluids in a safe manner. Similar steps may be taken to perform other processes on a sample using a unitary particle processing cartridge.

Figure 14:
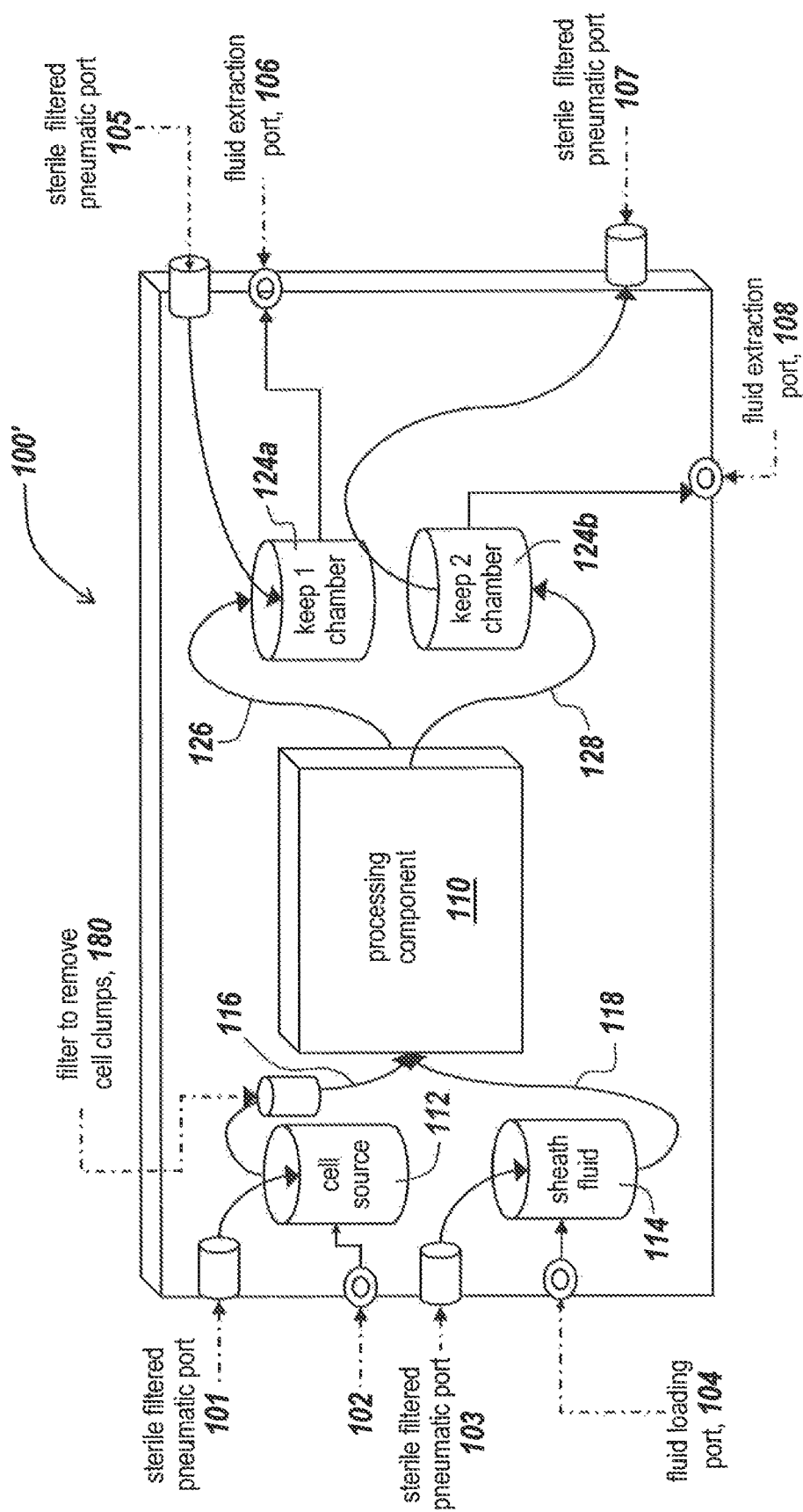
FIG. 14 illustrates a unitary particle sorting cartridge of an embodiment of the invention including an aggregation filter.

As shown in FIG. 14, a unitary particle processing cartridge 100' of an embodiment of the invention may include also an aggregation filter 180 to help remove clumps of cells and prevent clogging of the sorting component. As shown, the aggregation filter 180 can be added to the fluid line(s) 116 connecting the cell source 112 to the processing component 110. The aggregation filter 180 may comprise any suitable material suitable for filtering a sample and may be disposed in any location along a fluid flow path in the cartridge 100'.

Figure 15:
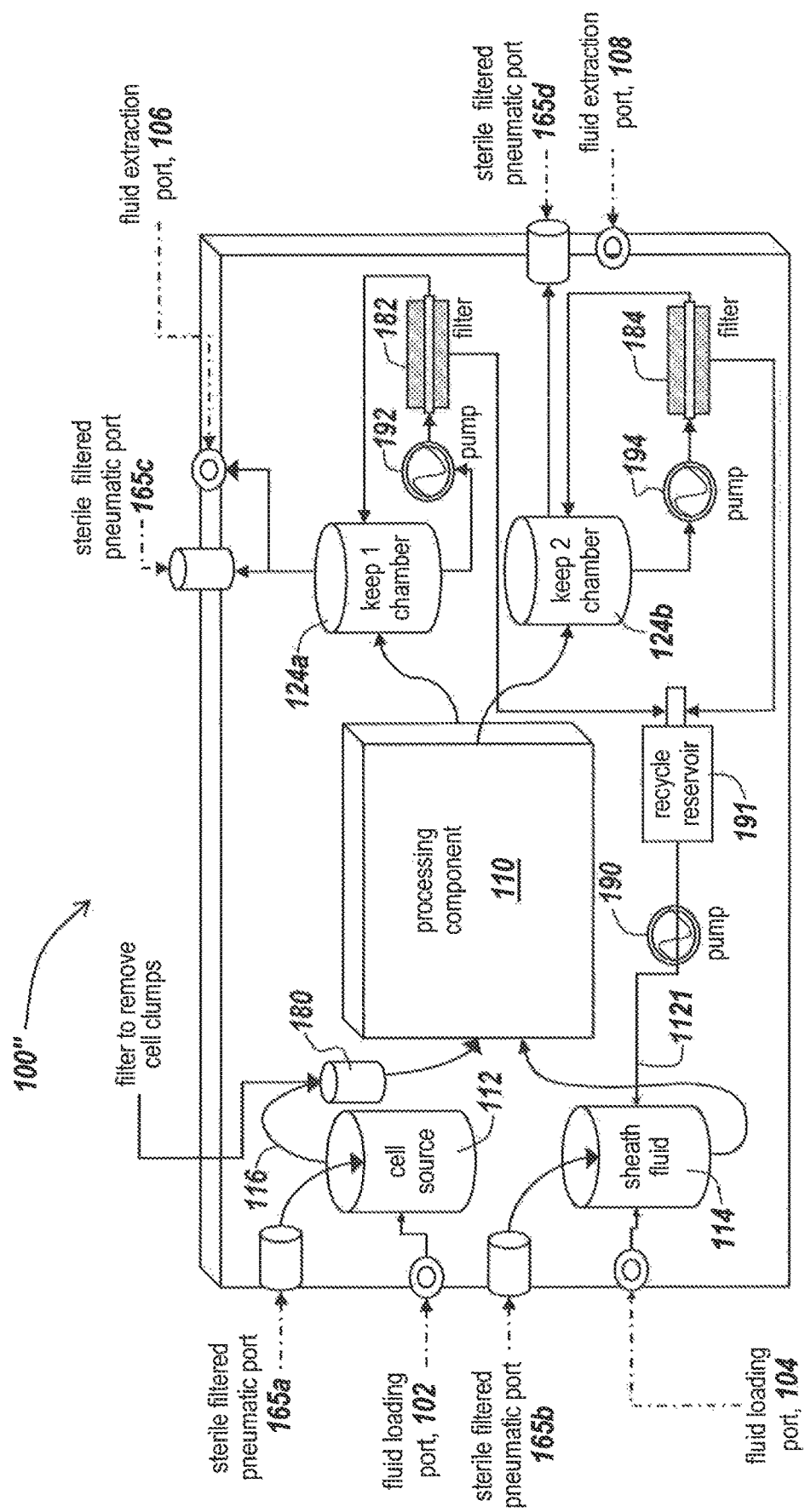
FIG. 15 illustrates a unitary particle sorting cartridge of another embodiment of the invention including pumps and filters for controlling liquid level and/or the concentration of sheath fluid, as well as providing sheath recycling.

As shown in FIG. 15, a unitary particle processing cartridge 100" of another embodiment of the invention may include a component for liquid level/concentration control and sheath recycling after performing particle processing using the processing component 110. The illustrative cartridge 100" includes a pump 192, 194 and a filter 182, 184 downstream of each processed particle chamber 124 a, 124 b, respectively, that receives processed particles from the processing component. The pumps 192 and 194 and filters 182, 184 facilitate liquid level/concentration control and recycling of a processing means, such as sheath fluid, used to process the particles. The filters 182, 184 maybe three-port flow filters, for example, hollow fiber filters, for removing fluid, such as sheath fluid, from a fluid path (i.e., the corresponding processed particle chamber 124). The system thus removes sheath fluid from the processed particle chambers to raise the concentration of collected particles in the processed particle chambers and to control the level of liquid in each processed particle chamber 124a, 124b.

The illustrative unitary particle processing cartridge 100" also includes a recycling component for recycling fluid collected by the filters 182, 184. As shown, the excess fluid may be recovered (recycled) and returned into the processing medium reservoir 114, for example, a sheath fluid reservoir, using a recycling path 1121, recycling reservoir 191 and a pump 190. The recycling reservoir 191 receives the removed fluid from the filters 182 and 184, and the pump 190 returns the extracted fluid from the filters 182 and 184 to the chamber to 114 via fluid path 1121 for reuse during subsequent particle processing procedures.

In general, a unitary particle processing cartridge of an illustrative embodiment of the invention is a single object sealed against liquid transfer either in or out of the cartridge, except at specific ports that are only used in a specific standard operating procedure (SOP) that guarantees that their use does not violate the isolation of the interior of the cartridge or leak interior samples into the exterior.

In one embodiment, the unitary particle processing cartridge is operated by being placed in a machine or system (the "Operating Machine") which may apply means of to actuation and sensing to the cartridge to perform one or more "unit process operations" on a suspension that has been loaded into the cartridge. The unit process operations performed using the cartridge may change the state of the suspension, measure some properties of the suspension, both change the state and measures selected properties of a suspension, or other perform another suitable process on a suspension loaded in the cartridge. Examples of unit processes suitable for use with the unitary cartridge of an illustrative embodiment of the invention include, but are not limited to, measuring the number of cells in a suspension, measuring the amount of liquid in a suspension, measuring the type of cells in a suspension, which may be a cytometry operation, sorting cells in the suspension, collecting a subset of the cells in a suspension, heating the cells in a suspension, filtering a suspension to increase the concentration of cells therein, and changing the liquid or its chemical components in a suspension.

The operating machine that operates on the unitary particle processing cartridge may use electrical, mechanical, pneumatic, optical, magnetic or other suitable actuation or sensing means known in the art to perform unit process operations on a suspension in the cartridge. Examples of actuation or sensing means suitable for use in an operating machine that employs the unitary cartridge of the illustrative embodiment of the invention include, but are not limited to, pneumatic means, mechanical means, optical means, magnetic means and electrical means. To actuate or sense using a pneumatic means, a gas may be injected through a sterile filter to drive a liquid suspension from one chamber to another or from a chamber through a component such as a size filter and into a second chamber. To actuate or sense using a mechanical means, a peristaltic pump head may be built into the cartridge so that an external rotor may fit into that head and by rotating it pump liquid or gas from one chamber to another. To actuate or sense using an optical means, a light beam may be disposed relative to the cartridge to pass through a microchannel in the cartridge in order to count cells or particles that pass through that microchannel and transiently block or scatter the light on its way to a photodetector. To actuate or sense using a magnetic means, a rotating magnet may be brought close to a chamber containing a conventional magnetic stir bar, causing that stir bar to rotate and stir or mix the suspension in that chamber. To actuate or sense using an electrical means, conventional silicon pressure or temperature sensors may be built into the cartridge and their electrical leads may be connected to through the means of external contact pins. The operating machine may then apply and read voltages to or from these contact pins to operate the sensors. Alternatively, using an electrical means, a data storage means, which may be part of a microcontroller or CPU, digital or analog, may be built into the cartridge if it is advisable for the cartridge itself to be given a logging function or intelligence function to support its use or standard operating procedures for handling the cartridge. Power for these devices may come from the operating machine or be derived from batteries or electrical power storage means located within the unitary cartridge. In another embodiment of a mechanical means for performing a process in a suspension loaded in a cartridge, two chambers may be connected by a tube with a region containing a soft wall to form a valve. Then, the operating machine may press on this region with a mechanical plate or other suitable means to temporarily or permanently crimp that region and selectively block liquid or gas flow from one chamber to another.

The use of the cartridge allows the operating machine to be isolated from and external to the processing subsystem and fluid contact surface. In this manner, the operating machine can be used repeatedly, while the fluid contact surfaces can be disposable.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and protected by Letters Patent is:

1. A particle processing assembly for sorting individual particles on a particle-by-particle basis from a stream of particles, the particle processing assembly comprising:
   a microfluidic chip including a plurality of microsorters, each microsorter having a switching region and a microfluidic channel formed in the microfluidic chip that is fluidically coupled to a sample input a keep output, a waste output, and the switching region,
   wherein the switching region of each microsorter interfaces with an actuator from a plurality of actuators external to the microfluidic chip, and
   wherein each of the respective switching regions, when actuated by a respective one of the actuators upon detection of a predetermined characteristic of a selected particle in a respective one of the microfluidic channels of a respective one of the microsorters, directs a pressure pulse across the respective one of the microfluidic channels to deflect the selected particle from the stream of particles.

2. The particle processing assembly of claim 1, further comprising:
   a cartridge having fluid contact surfaces including a sample chamber, a keep chamber and a waste chamber, wherein the sample chamber of the cartridge is in fluid communication with the sample input of each of the microsorters, wherein the keep chamber of the cartridge is in fluid communication with the keep output of each of the microsorters, wherein the waste chamber of the cartridge is in fluid communication with the waste output of each of the microsorters, and
   wherein all the fluid contact surfaces of the particle processing assembly are enclosed and configured to be sealed against liquid transfer to an exterior environment during a sorting operation.

3. The particle processing assembly of claim 2, wherein the cartridge includes a sorted sample extraction port in fluid communication with the keep chamber and configured to be unsealed after the sorting operation has ended to provide access to fluid within the keep chamber.

4. The particle processing assembly of claim 2, wherein all the fluid contact surfaces needed for the sorting operation are enclosed within the particle processing assembly.

5. The particle processing assembly of claim 2, wherein the particle processing assembly is configured to allow pressurized air to drive the stream of particles through the microfluidic channel.

6. The particle processing assembly of claim 2, wherein the fluid contact surfaces of the cartridge include a sheath chamber configured to supply sheath fluid to each of the plurality of microsorters upstream of the switching region for that microsorter.

7. The particle processing assembly of claim 2, wherein the microfluidic chip and the cartridge are provided as a unitary particle processing cartridge assembly.

8. The particle processing assembly of claim 7, wherein the unitary particle processing cartridge assembly is a rigid and integral assembly.

9. The particle processing assembly of claim 1, wherein each of the microfluidic channels includes a detection region wherein particle characteristics of individual particles of a sample are detected on a particle-by-particle basis during the sorting operation.

10. The particle processing assembly of claim 1, wherein the particle processing assembly includes a unique identifier.

11. A system for sorting individual particles on a particle-by-particle basis from a plurality of streams of particles, the system comprising:
    a particle processing assembly including a microfluidic chip, the microfluidic chip including a plurality of microsorters, each of the microsorters having a switching region and a microfluidic channel formed in the microfluidic chip that is fluidically coupled to a sample input a keep output, a waste output, and the switching region; and a plurality of actuators, each actuator in the plurality of actuators associated with a respective one of the plurality of microsorters and configured to generate a pressure pulse in the switching region of the respective microfluidic channel of the associated microsorter, wherein each of the switching regions is capable of directing the pressure pulse generated by the associated one of the actuators to deflect a selected particle from a selected one of the streams of particles, and wherein each of the actuators in the plurality of actuators is external to the particle processing assembly and is interfaced with the switching region of a respective one of the microsorters and wherein each of the actuators in the plurality of actuators is configured to be actuated in response to a desired particle characteristic of an individual particle being detected in a detection region of a respective one of the microsorters.

12. The system of claim 11, wherein the particle processing assembly further includes a cartridge having fluid contact surfaces including a sample chamber, a keep chamber and a waste chamber, wherein the sample chamber of the cartridge is in fluid communication with the sample input of each of the microsorters, wherein the keep chamber of the cartridge is in fluid communication with the keep output of each of the microsorters, wherein the waste chamber of the cartridge is in fluid communication with the waste output of each of the microsorters, and wherein all the fluid contact surfaces of the particle processing assembly are enclosed and configured to be sealed against liquid transfer to an exterior environment during a sorting operation.

13. The system of claim 11, wherein each actuator in the plurality of actuators is configured to supply at least one of a mechanical, electrical, pneumatic or magnetic force to at least one switch element associated with the switching region corresponding to that actuator.

14. The system of claim 11, wherein the operative interface between each actuator in the plurality of actuators and the switching region of the associated microsorter includes a pre-stressed state between each actuator and the particle processing assembly.

15. A method for sorting particles comprising:

obtaining a microfluidic particle sorting component including a plurality of microsorters, each of the microsorters having a switching region and a microfluidic channel formed in the microfluidic chip that is fluidically coupled to a sample input, a keep output, a waste output, and the switching region;

operatively interfacing the microfluidic particle sorting component with an operating machine, including aligning the switching region of each of the microsorters in the microfluidic particle sorting component with a corresponding pressure pulse generator external to the microfluidic particle sorting component and provided by the operating machine;

operating the operating machine to process a sample having particles to be sorted, including the steps of:
 flowing the sample containing particles through the microfluidic particle sorting component;
 detecting whether individual particles flowing within one of the microsorters in the plurality of microsorters in the microfluidic particle sorting component have a predetermined characteristic;
 causing the pressure pulse generator provided on the operating machine to generate a pressure pulse in the corresponding switching region of the associated microsorter in response to the predetermined characteristic of an individual particle being detected;
 deflecting the individual particle from the particles flowing within the microfluidic particle sorting component into one of the keep output and the waste output of the associated microsorter; and removing the microfluidic particle sorting component from the operating machine.

16. The method of claim 15, further including the steps:

providing the microfluidic particle sorting component as part of a cartridge assembly, the cartridge assembly having internal fluid contact surfaces including a sample fluid input reservoir and a selected particle fluid output reservoir;

loading a sample containing particles into the sample fluid input reservoir of the cartridge assembly via a sealable sample input port; and sealing the cartridge assembly against liquid transfer into and out of the cartridge assembly.

17. The method of claim 16, wherein the cartridge assembly remains sealed during the steps of operatively interfacing, operating, and removing, and wherein all fluid contact surfaces required for a microfluidic particle sorting operation are enclosed by the cartridge assembly and are isolated from exposure to an exterior environment during the microfluidic particle sorting operation.

18. The method of claim 16, further comprising:

extracting a sample containing selected particles from the selected particle fluid output reservoir of the cartridge assembly via a processed sample output port.

19. The particle processing assembly of claim 1, further comprising:

a cartridge having fluid contact surfaces including a sample chamber, a first keep chamber, a second keep chamber, and a waste chamber, wherein the sample chamber of the cartridge is in fluid communication with the sample input of each of the microsorters, wherein the first keep chamber of the cartridge is in fluid communication with the keep output of a first group of the microsorters and the second keep chamber of the cartridge is in fluid communication with the keep output of a second group of the microsorters, wherein the waste chamber of the cartridge is in fluid communication with the waste output of each of the microsorters, and wherein all the fluid contact surfaces of the particle processing assembly are enclosed and configured to be sealed against liquid transfer to an exterior environment during a sorting operation.

20. The system of claim 11, further comprising:

wherein the particle processing assembly further includes a cartridge having fluid contact surfaces including a sample chamber, a first keep chamber, a second keep chamber, and a waste chamber, wherein the sample chamber of the cartridge is in fluid communication with the sample input of each of the microsorters, wherein the first keep chamber of the cartridge is in fluid communication with the keep output of a first group of the microsorters and the second keep chamber of the cartridge is in fluid communication with the keep output of a second group of the microsorters, wherein the waste chamber of the cartridge is in fluid communication with the waste output of each of the microsorters, and wherein all the fluid contact surfaces of the particle processing assembly are enclosed and configured to be sealed against liquid transfer to an exterior environment during a sorting operation.

\* \* \* \* \*